(12) United States Patent
Scheller et al.

(10) Patent No.: US 10,011,813 B2
(45) Date of Patent: Jul. 3, 2018

(54) METHANE OXIDATION METHODS AND COMPOSITIONS

(71) Applicant: California Institute of Technology, Pasadena, CA (US)

(72) Inventors: Silvan Scheller, Zurich (CH); Victoria J. Orphan, Pasadena, CA (US); Hang Yu, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 28 days.

(21) Appl. No.: 15/294,704

(22) Filed: Oct. 15, 2016

(65) Prior Publication Data

US 2017/0107479 A1    Apr. 20, 2017

Related U.S. Application Data

(60) Provisional application No. 62/242,420, filed on Oct. 16, 2015.

(51) Int. Cl.

| H01M 8/04 | (2016.01) |
|---|---|
| C12M 1/00 | (2006.01) |
| C12M 1/12 | (2006.01) |
| H01M 4/92 | (2006.01) |
| H01M 8/06 | (2016.01) |
| H01M 8/1009 | (2016.01) |
| H01M 8/1039 | (2016.01) |
| H01M 8/1018 | (2016.01) |

(52) U.S. Cl.
CPC ............ *C12M 43/08* (2013.01); *C12M 25/02* (2013.01); *C12M 29/00* (2013.01); *C12M 29/04* (2013.01); *C12M 29/20* (2013.01); *C12M 29/26* (2013.01); *H01M 4/921* (2013.01); *H01M 4/925* (2013.01); *H01M 8/06* (2013.01); *H01M 8/1009* (2013.01); *H01M 8/1039* (2013.01); *H01M 2008/1095* (2013.01)

(58) Field of Classification Search
CPC ...................................................... H01M 8/04
See application file for complete search history.

(56) References Cited

U.S. PATENT DOCUMENTS

| 2011/0076519 A1 | 3/2011 | Chandran et al. |
| 2011/0123835 A1* | 5/2011 | Girguis ............... H01M 8/16 429/2 |
| 2011/0300411 A1 | 12/2011 | Materi |
| 2014/0188282 A1 | 7/2014 | West |

FOREIGN PATENT DOCUMENTS

WO    2014/144705 A2    9/2014

OTHER PUBLICATIONS

Cohen, Y., "Biofiltration—the treatment of fluids by microorganisms immobilized into the filter bedding material: a review," Bioresource Technology, Jan. 10, 2001, vol. 77, No. 3, pp. 257-274.

(Continued)

*Primary Examiner* — Olatunji Godo
(74) *Attorney, Agent, or Firm* — Gavrilovich, Dodd & Lindsey LLP

(57) ABSTRACT

The disclosure provides devices and methods to produce electrical energy from microorganisms capable of metabolizing methane.

19 Claims, 20 Drawing Sheets

(56) References Cited

OTHER PUBLICATIONS

Copenheaver, Blaine R., International Search Report and Written Opinion, PCT/US2016/057246, U.S. Patent and Trademark Office, dated Jan. 24, 2017.

Evelyn, E., "Mediator Combined Gaseous Substrate for Electricity Generation in Microbial Fuel Cells (MFCs) and Potential Integration of a MFC into an Anaerobic Biofiltration System," University of Canterbury College of Engineering, 2013, pp. 1-178, Retrieved from the Internet: <https://ir.canterbury.ac.nz/bitstream/handle/10092/10733/Thesis_Evelyn.pdf> on Dec. 15, 2016.

Van Hees, W., "A bacterial methane fuel cell," Journal of the Electrochemical Society, 1965, vol. 112, No. 3, pp. 258-262.

\* cited by examiner

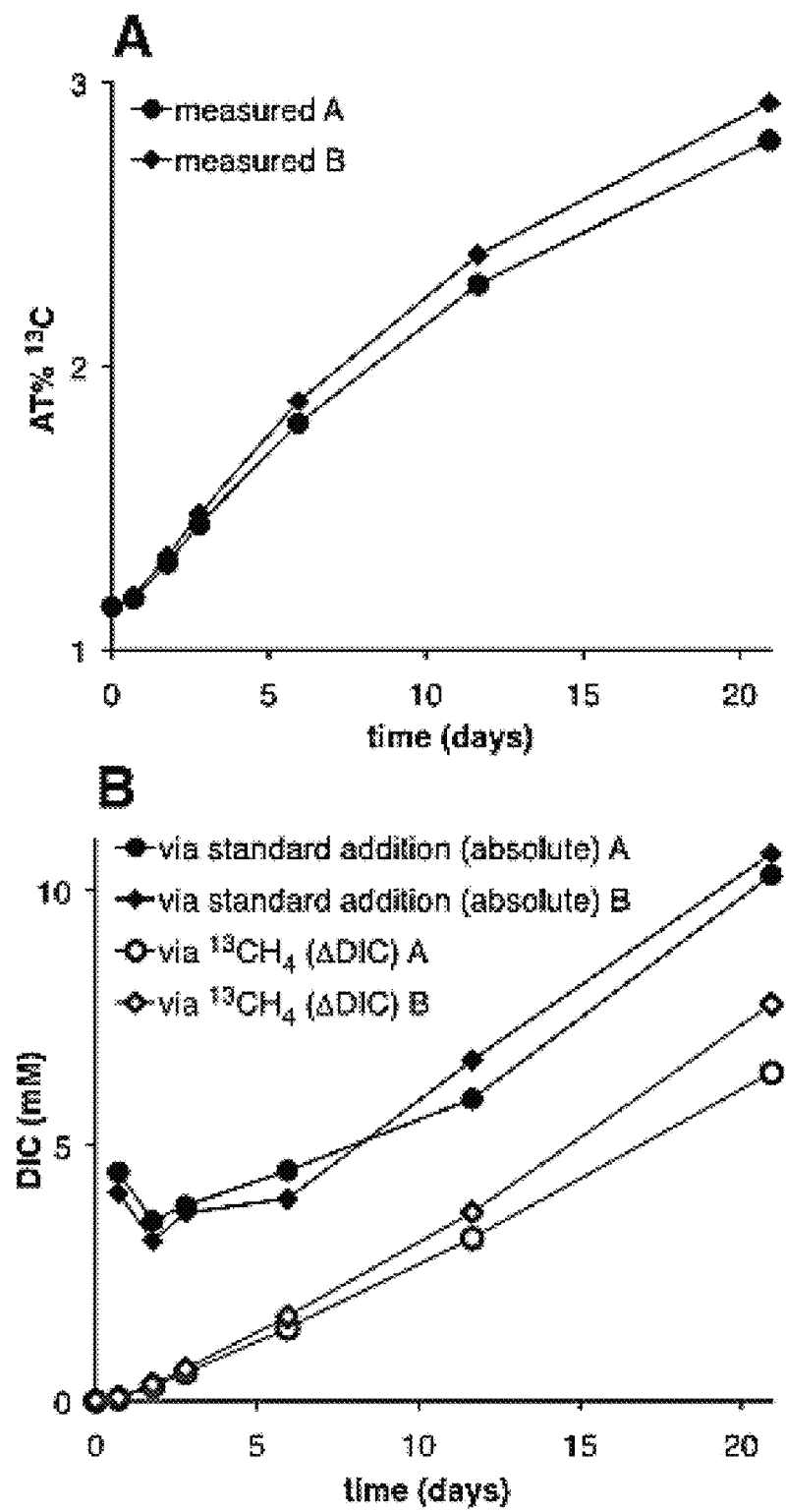
*FIG. 3A-B*

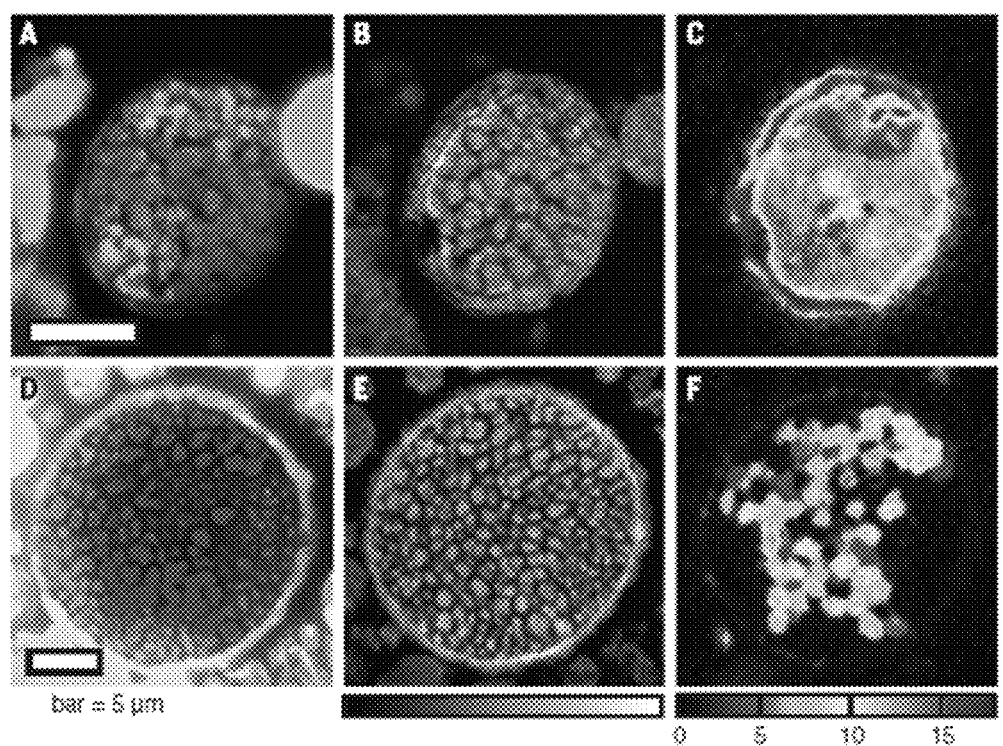
FIG. 7A-F
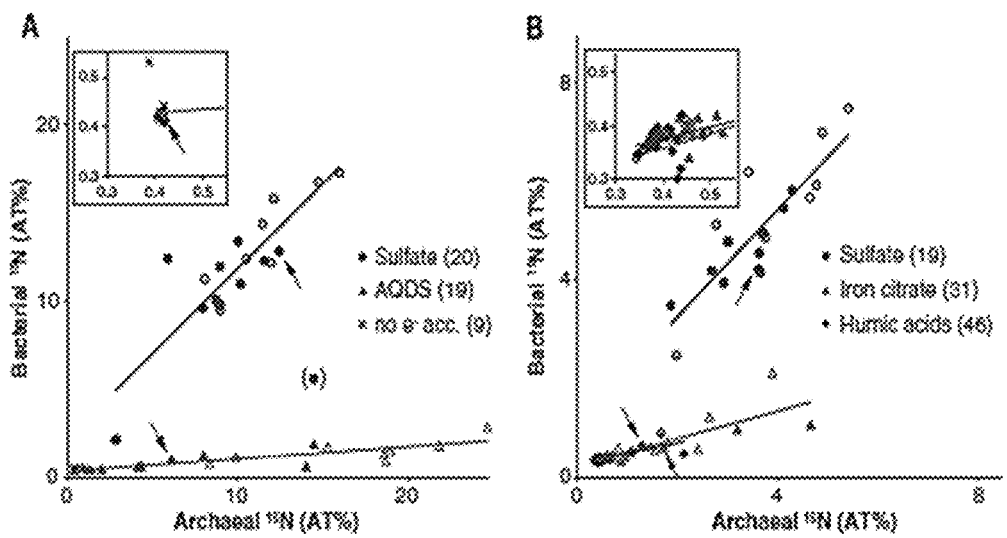
FIG. 8A-B

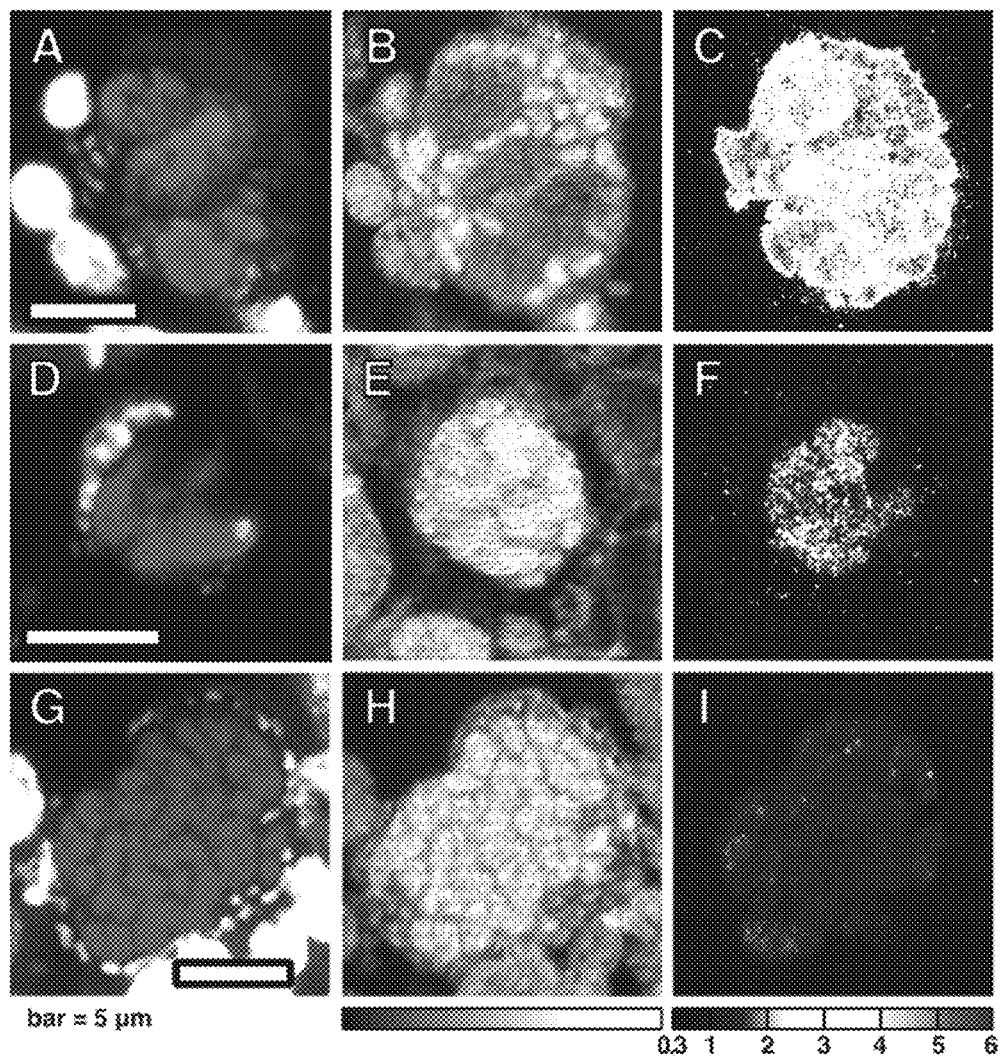
FIG. 9A-I

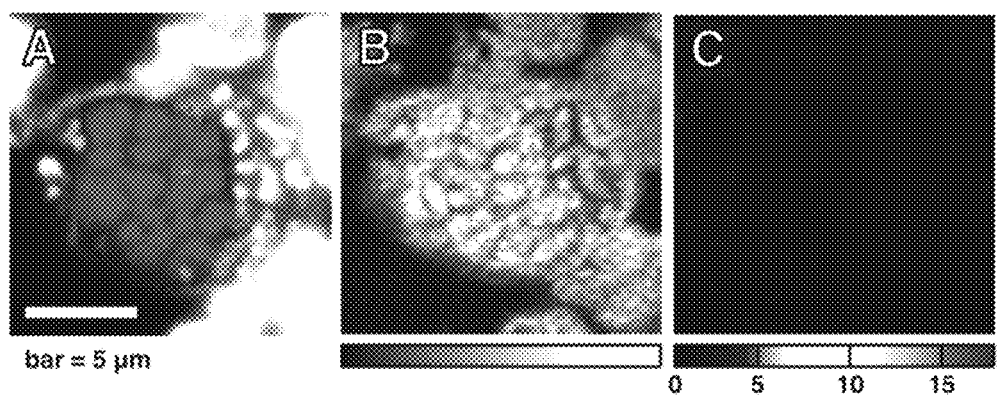
FIG. 10A-C
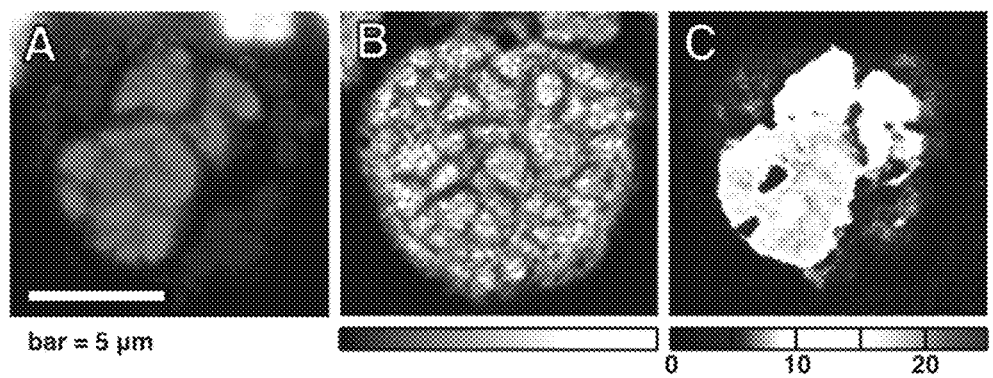
FIG. 11A-C

| no | ANME | a $^{14}$N counts | a $^{15}$N counts | b $^{14}$N counts | b $^{15}$N counts | a $^{15}$N fraction | b $^{15}$N fraction |
|---|---|---|---|---|---|---|---|
| Set 1: Sulfate | | | | | | | |
| 1 | 2c | 8186903 | 910346 | 4986312 | 770403 | 0.1001 | 0.1338 |
| 2* | 2c | 13234012 | 2228293 | 9988379 | 591393 | 0.1441 | 0.0559 |
| 3 | 2c | 1017392 | 100206 | 4734445 | 514724 | 0.0897 | 0.0981 |
| 4 | other | 10447750 | 1350011 | 16572950 | 2779724 | 0.1144 | 0.1436 |
| 5 | 2c | 2896866 | 327406 | 4306194 | 530991 | 0.1015 | 0.1098 |
| 6 | other | 5173791 | 509800 | 10152972 | 1060263 | 0.0897 | 0.0946 |
| 7 | 2c | 8069719 | 1053146 | 10253054 | 1436464 | 0.1154 | 0.1229 |
| 8 | other | 9548875 | 1646186 | 11052811 | 2226646 | 0.1470 | 0.1677 |
| 9 | 2c | 15412698 | 1470548 | 7454752 | 836300 | 0.0871 | 0.1009 |
| 10 | other | 1254227 | 172559 | 434489 | 81620 | 0.1209 | 0.1581 |
| 11 | other | 523351 | 45850 | 455947 | 57855 | 0.0806 | 0.1126 |
| 12 | 2c | 586645 | 57716 | 467545 | 63416 | 0.0896 | 0.1194 |
| 13 | 2c | 9284639 | 274089 | 992128 | 22318 | 0.0287 | 0.0220 |
| 14 | other | 13355485 | 2529941 | 10646441 | 2223613 | 0.1593 | 0.1728 |
| 15 | 2c | 8150920 | 509359 | 7548831 | 1069396 | 0.0588 | 0.1241 |
| 16 | 2c | 9090606 | 1285688 | 3806417 | 560889 | 0.1239 | 0.1284 |
| 17 | 2c | 4446504 | 383623 | 2105270 | 223125 | 0.0794 | 0.0958 |
| 18 | other | 6543141 | 886483 | 4962457 | 687646 | 0.1193 | 0.1217 |
| 19 | other | 5192683 | 506817 | 3032520 | 326993 | 0.0889 | 0.0973 |
| 20 | other | 4772514 | 558378 | 5406186 | 765379 | 0.1047 | 0.1240 |

*FIG. 12*

| no | ANME | a $^{14}$N counts | a $^{15}$N counts | b $^{14}$N counts | b $^{15}$N counts | a $^{15}$N fraction | b $^{15}$N fraction |
|---|---|---|---|---|---|---|---|
| Set 1: AQDS | | | | | | | |
| 1 | 2c | 6072396 | 126268 | 3174807 | 14796 | 0.0204 | 0.0046 |
| 2 | 2c | 6738562 | 291479 | 2337765 | 15076 | 0.0415 | 0.0064 |
| 3 | 2c | 4174136 | 678303 | 6944724 | 45479 | 0.1398 | 0.0065 |
| 4 | 2c | 4421657 | 39358 | 3701860 | 21362 | 0.0088 | 0.0057 |
| 5 | 2c | 9024087 | 1521364 | 2290624 | 45313 | 0.1443 | 0.0194 |
| 6 | other | 12497523 | 3481819 | 1829789 | 34577 | 0.2179 | 0.0185 |
| 7 | other | 14933629 | 1359298 | 5258297 | 43004 | 0.0834 | 0.0081 |
| 8 | other | 34700825 | 3797466 | 14097837 | 164882 | 0.0986 | 0.0116 |
| 9 | 2c | 1400937 | 5689 | 1219111 | 5187 | 0.0040 | 0.0042 |
| 10 | other | 4102974 | 1339454 | 656114 | 19576 | 0.2461 | 0.0290 |
| 11 | 2c | 1932351 | 87738 | 2609306 | 17195 | 0.0434 | 0.0065 |
| 12 | 2c | 5872808 | 85174 | 11129659 | 48086 | 0.0143 | 0.0043 |
| 13 | 2c | 21909385 | 1429092 | 16271732 | 172963 | 0.0612 | 0.0105 |
| 14 | 2c | 25267632 | 301796 | 14219942 | 66618 | 0.0118 | 0.0047 |
| 15 | other | 5632270 | 1292904 | 2895095 | 27853 | 0.1867 | 0.0095 |
| 16 | other | 27058715 | 4864118 | 7520936 | 135132 | 0.1524 | 0.0177 |
| 17 | other | 18133896 | 4135568 | 10299199 | 145195 | 0.1857 | 0.0139 |
| 18 | other | 23419015 | 5468125 | 7276084 | 112843 | 0.1893 | 0.0153 |
| 19 | 2c | 29832362 | 2586694 | 10923964 | 142677 | 0.0798 | 0.0129 |

| no | ANME | a $^{14}$N counts | a $^{15}$N counts | b $^{14}$N counts | b $^{15}$N counts | a $^{15}$N fraction | b $^{15}$N fraction |
|---|---|---|---|---|---|---|---|
| Set 1: no oxidant | | | | | | | |
| 1 | other | 27743268 | 116427 | 26164833 | 108451 | 0.0042 | 0.0041 |
| 2 | other | 10368296 | 44295 | 5406673 | 22582 | 0.0043 | 0.0042 |
| 3 | 2c | 5725992 | 23424 | 2571274 | 10786 | 0.0041 | 0.0042 |
| 4 | 2c | 2337391 | 9594 | 1496614 | 6431 | 0.0041 | 0.0043 |
| 5 | 2c | 4006009 | 16847 | 2432421 | 10715 | 0.0042 | 0.0044 |
| 6 | 2c | 796822 | 3103 | 637887 | 3373 | 0.0039 | 0.0053 |
| 7 | other | 2168580 | 9002 | 913893 | 3964 | 0.0041 | 0.0043 |
| 8 | other | 2027340 | 8569 | 533112 | 2280 | 0.0042 | 0.0043 |
| 9 | 2c | 594977 | 2510 | 250708 | 1120 | 0.0042 | 0.0044 |

*FIG. 12 (Cont'd)*

| no | ANME | a $^{14}$N counts | a $^{15}$N counts | b $^{14}$N counts | b $^{15}$N counts | a $^{15}$N fraction | b $^{15}$N fraction |
|---|---|---|---|---|---|---|---|
| Set 2: Sulfate | | | | | | | |
| 1 | 2c | 8087694 | 305021 | 9201606 | 439261 | 0.0363 | 0.0456 |
| 2 | 2c | 14667860 | 628799 | 5998433 | 346787 | 0.0411 | 0.0547 |
| 3 | 2c | 15123316 | 455273 | 15751906 | 646736 | 0.0292 | 0.0394 |
| 4 | 2c | 6143931 | 236920 | 5971520 | 312392 | 0.0371 | 0.0497 |
| 5 | other | 6096641 | 123600 | 5619590 | 142946 | 0.0199 | 0.0248 |
| 6 | other | 910494 | 32272 | 655354 | 43321 | 0.0342 | 0.0620 |
| 7 | 2c | 4214918 | 158386 | 9693657 | 426387 | 0.0362 | 0.0421 |
| 8 | other | 33488023 | 1268969 | 15216001 | 658815 | 0.0365 | 0.0415 |
| 9 | 2c | 11309440 | 214881 | 7779576 | 280883 | 0.0186 | 0.0348 |
| 10 | other | 15482854 | 594463 | 5301457 | 275310 | 0.0370 | 0.0494 |
| 11 | other | 1786420 | 91861 | 1233988 | 92978 | 0.0489 | 0.0701 |
| 12 | 2c | 9145651 | 409931 | 3955885 | 244739 | 0.0429 | 0.0583 |
| 13 | 2c | 3867661 | 107011 | 1599231 | 69821 | 0.0269 | 0.0418 |
| 14 | other | 50990162 | 2917348 | 27076729 | 2189768 | 0.0541 | 0.0748 |
| 15 | other | 8328778 | 405356 | 7942316 | 478070 | 0.0464 | 0.0568 |
| 16 | 2c | 36187900 | 1123734 | 15598271 | 783987 | 0.0301 | 0.0479 |
| 17 | other | 118836163 | 3398649 | 24451232 | 1322277 | 0.0278 | 0.0513 |
| 18 | other | 12972873 | 507426 | 16102047 | 823092 | 0.0376 | 0.0486 |
| 19 | other | 14351082 | 718547 | 5907655 | 372495 | 0.0477 | 0.0593 |

FIG. 12 (Cont'd)

| no | ANME | a $^{14}$N counts | a $^{15}$N counts | b $^{14}$N counts | b $^{15}$N counts | a $^{15}$N fraction | b $^{15}$N fraction |
|---|---|---|---|---|---|---|---|
| Set 2: Fe$^{III}$-citrate | | | | | | | |
| 1 | other | 13958433 | 256405 | 2142551 | 15908 | 0.0180 | 0.0074 |
| 2 | 2c | 80658680 | 426938 | 40755590 | 159073 | 0.0053 | 0.0039 |
| 3 | 2c | 7945594 | 76309 | 2466373 | 10663 | 0.0095 | 0.0043 |
| 4 | 2c | 25346261 | 103012 | 30689462 | 121272 | 0.0040 | 0.0039 |
| 5 | 2c | 24940312 | 115912 | 9047431 | 35106 | 0.0046 | 0.0039 |
| 6 | 2c | 28445673 | 128781 | 7571431 | 30020 | 0.0045 | 0.0039 |
| 7 | 2c | 17070092 | 79021 | 10395414 | 42311 | 0.0046 | 0.0041 |
| 8 | 2c | 33377158 | 145571 | 26132592 | 108667 | 0.0043 | 0.0041 |
| 9 | other | 11158319 | 82807 | 4238780 | 18974 | 0.0074 | 0.0045 |
| 10 | 2c | 90768537 | 415556 | 32521432 | 111492 | 0.0046 | 0.0034 |
| 11 | other | 5730271 | 84783 | 4685776 | 29842 | 0.0146 | 0.0063 |
| 12 | other | 1771637 | 9949 | 734437 | 3142 | 0.0056 | 0.0043 |
| 13 | 2c | 1079883 | 7359 | 672707 | 2715 | 0.0068 | 0.0040 |
| 14 | 2c | 13358256 | 63664 | 5039684 | 20964 | 0.0047 | 0.0041 |
| 15 | 2c | 521199 | 5641 | 421875 | 2195 | 0.0107 | 0.0052 |
| 16 | other | 12034615 | 487803 | 4495900 | 97325 | 0.0390 | 0.0212 |
| 17 | other | 67354991 | 648685 | 23031378 | 98321 | 0.0095 | 0.0043 |
| 18 | 2c | 26683636 | 137727 | 18050449 | 76041 | 0.0051 | 0.0042 |
| 19 | other | 34660589 | 858122 | 5156201 | 30589 | 0.0242 | 0.0059 |
| 20 | 2c | 2726245 | 10646 | 1167407 | 4668 | 0.0039 | 0.0040 |
| 21 | other | 12633567 | 103769 | 3697589 | 23008 | 0.0081 | 0.0062 |
| 22 | 2c | 1582971 | 9352 | 741502 | 3509 | 0.0059 | 0.0047 |
| 23 | other | 80592797 | 1264580 | 47868634 | 266877 | 0.0154 | 0.0055 |
| 24 | other | 7272802 | 197358 | 1815950 | 22945 | 0.0264 | 0.0125 |
| 25 | 2c | 726949 | 3227 | 869859 | 3359 | 0.0044 | 0.0038 |
| 26 | other | 10556506 | 59782 | 2868653 | 11472 | 0.0056 | 0.0040 |
| 27 | 2c | 3799183 | 66454 | 753031 | 4718 | 0.0172 | 0.0062 |
| 28 | 2c | 249351 | 8235 | 159039 | 1582 | 0.0320 | 0.0098 |
| 29 | 2c | 17565368 | 858385 | 8662755 | 94449 | 0.0466 | 0.0108 |
| 30 | 2c | 4004142 | 16716 | 1971058 | 7616 | 0.0042 | 0.0038 |
| 31 | 2c | 26175206 | 229809 | 10609375 | 36439 | 0.0087 | 0.0034 |

*FIG. 12 (Cont'd)*

| no | ANME | a $^{14}$N counts | a $^{15}$N counts | b $^{14}$N counts | b $^{15}$N counts | a $^{15}$N fraction | b $^{15}$N fraction |
|---|---|---|---|---|---|---|---|
| Set 2: Humic acids | | | | | | | |
| 1 | other | 55117751 | 205562 | 33614478 | 126802 | 0.0037 | 0.0038 |
| 2 | 2c | 25490787 | 110116 | 16573079 | 62509 | 0.0043 | 0.0038 |
| 3 | 2c | 16355923 | 62061 | 11353534 | 42632 | 0.0038 | 0.0037 |
| 4 | 2c | 1714610 | 7232 | 2068626 | 7368 | 0.0042 | 0.0035 |
| 5 | 2c | 15484727 | 68166 | 7298135 | 23485 | 0.0044 | 0.0032 |
| 6 | other | 27861590 | 191027 | 5821760 | 25592 | 0.0068 | 0.0044 |
| 7 | other | 21308772 | 78013 | 9206680 | 33601 | 0.0036 | 0.0036 |
| 8 | 2c | 5096678 | 18894 | 1266090 | 4568 | 0.0037 | 0.0036 |
| 9 | other | 51484560 | 184292 | 30993892 | 110596 | 0.0036 | 0.0036 |
| 10 | other | 60947497 | 220325 | 28581153 | 101978 | 0.0036 | 0.0036 |
| 11 | 2c | 8698946 | 32672 | 7242871 | 26593 | 0.0037 | 0.0037 |
| 12 | 2c | 1706409 | 6586 | 4794201 | 17402 | 0.0038 | 0.0036 |
| 13 | other | 25317446 | 96727 | 7293172 | 27065 | 0.0038 | 0.0037 |
| 14 | 2c | 3012438 | 65659 | 1078289 | 5336 | 0.0213 | 0.0049 |
| 15 | 2c | 1589700 | 17382 | 132418 | 727 | 0.0108 | 0.0055 |
| 16 | 2c | 2982865 | 10376 | 2787514 | 9735 | 0.0035 | 0.0035 |
| 17 | other | 12071094 | 204435 | 3823404 | 35601 | 0.0167 | 0.0092 |
| 18 | 2c | 62533691 | 257650 | 29351492 | 116502 | 0.0041 | 0.0040 |
| 19 | other | 4661401 | 18127 | 3330721 | 12872 | 0.0039 | 0.0038 |
| 20 | 2c | 1411693 | 5478 | 994683 | 3947 | 0.0039 | 0.0040 |
| 21 | 2c | 12452346 | 48188 | 10019896 | 37442 | 0.0039 | 0.0037 |
| 22 | 2c | 2756054 | 13427 | 2934052 | 11289 | 0.0048 | 0.0038 |
| 23 | other | 2230184 | 10036 | 1424952 | 5890 | 0.0045 | 0.0041 |
| 24 | other | 25175520 | 113101 | 9529710 | 38242 | 0.0045 | 0.0040 |

FIG. 12 (Cont'd)

| no | ANME | a $^{14}N$ counts | a $^{15}N$ counts | b $^{14}N$ counts | b $^{15}N$ counts | a $^{15}N$ fraction | b $^{15}N$ fraction |
|---|---|---|---|---|---|---|---|
| Set 2: Humic acids (cont'd) | | | | | | | |
| 25 | other | 46314144 | 230182 | 13121757 | 51152 | 0.0049 | 0.0039 |
| 26 | other | 30810467 | 118178 | 21636937 | 80911 | 0.0038 | 0.0037 |
| 27 | other | 25912507 | 101075 | 25529653 | 95841 | 0.0039 | 0.0037 |
| 28 | 2c | 6613731 | 27686 | 1335995 | 5250 | 0.0042 | 0.0039 |
| 29 | 2c | 2821470 | 10703 | 494632 | 1923 | 0.0038 | 0.0039 |
| 30 | 2c | 32229781 | 121891 | 12349381 | 46419 | 0.0038 | 0.0037 |
| 31 | 2c | 29021850 | 128491 | 15403182 | 64994 | 0.0044 | 0.0042 |
| 32 | 2c | 13268313 | 51047 | 3640947 | 13699 | 0.0038 | 0.0037 |
| 33 | 2c | 3919208 | 24209 | 942992 | 3784 | 0.0061 | 0.0040 |
| 34 | other | 4830697 | 20192 | 1996265 | 7515 | 0.0042 | 0.0038 |
| 35 | 2c | 105728195 | 1376562 | 16280903 | 106545 | 0.0129 | 0.0065 |
| 36 | other | 27989361 | 109408 | 20585970 | 78464 | 0.0039 | 0.0038 |
| 37 | other | 35846128 | 139036 | 5793441 | 22969 | 0.0039 | 0.0039 |
| 38 | other | 21421209 | 82112 | 23012457 | 86891 | 0.0038 | 0.0038 |
| 39 | other | 48875263 | 168401 | 54750403 | 186101 | 0.0034 | 0.0034 |
| 40 | other | 49043583 | 188027 | 6873982 | 25469 | 0.0038 | 0.0037 |
| 41 | 2c | 2307701 | 8846 | 630923 | 2289 | 0.0038 | 0.0036 |
| 42 | other | 40320950 | 154632 | 18812307 | 71445 | 0.0038 | 0.0038 |
| 43 | 2c | 20353901 | 81696 | 9496510 | 36161 | 0.0040 | 0.0038 |
| 44 | 2c | 72837724 | 316207 | 27141409 | 82236 | 0.0043 | 0.0030 |
| 45 | other | 18002993 | 66271 | 8274426 | 30362 | 0.0037 | 0.0037 |
| 46 | 2c | 17935549 | 70220 | 10335920 | 40134 | 0.0039 | 0.0039 |

FIG. 12 (Cont'd)

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: mcrA ME1 primer

<400> SEQUENCE: 1
gcmatgcara thggwatgtc                                              20

<210> SEQ ID NO 2
<211> LENGTH: 21
<212> TYPE: DNA
<213> ORGANISM: Artificial Sequence
<220> FEATURE:
<223> OTHER INFORMATION: mcrA ME2 primer

<400> SEQUENCE: 2
tcatkgcrta gttdggrtag t                                            21

<210> SEQ ID NO 3
<211> LENGTH: 20
<212> TYPE: DNA
<213> ORGANISM: Artificial Sequence
<220> FEATURE:
<223> OTHER INFORMATION: 16S rRNA primer Arc23F

<400> SEQUENCE: 3
ttccggttga tccygccgga                                              20

<210> SEQ ID NO 4
<211> LENGTH: 18
<212> TYPE: DNA
<213> ORGANISM: Artificial Sequence
<220> FEATURE:
<223> OTHER INFORMATION: Bac27F primer

<400> SEQUENCE: 4
agagtttgat ymtggctc                                                18

<210> SEQ ID NO 5
<211> LENGTH: 19
<212> TYPE: DNA
<213> ORGANISM: Artificial Sequence
<220> FEATURE:
<223> OTHER INFORMATION: U1492R primer

<400> SEQUENCE: 5
```

-continued

```
ggytaccttg ttacgactt                                              19

<210> SEQ ID NO 6
<211> LENGTH: 16
<212> TYPE: DNA
<213> ORGANISM: Artificial Sequence
<220> FEATURE:
<223> OTHER INFORMATION: M13F primer

<400> SEQUENCE: 6
gtaaaacgac ggccag                                                 16

<210> SEQ ID NO 7
<211> LENGTH: 17
<212> TYPE: DNA
<213> ORGANISM: Artificial Sequence
<220> FEATURE:
<223> OTHER INFORMATION: M13R primer

<400> SEQUENCE: 7
caggaaacag ctatgac                                                17

<210> SEQ ID NO 8
<211> LENGTH: 20
<212> TYPE: DNA
<213> ORGANISM: Artificial Sequence
<220> FEATURE:
<223> OTHER INFORMATION: FISH probe

<400> SEQUENCE: 8
gtgctccccc gccaattcct                                             20

<210> SEQ ID NO 9
<211> LENGTH: 18
<212> TYPE: DNA
<213> ORGANISM: Artificial Sequence
<220> FEATURE:
<223> OTHER INFORMATION: FISH probe

<400> SEQUENCE: 9
cgcccccagc tttcgtcc                                               18

<210> SEQ ID NO 10
<211> LENGTH: 18
<212> TYPE: DNA
<213> ORGANISM: Artificial Sequence
<220> FEATURE:
<223> OTHER INFORMATION: FISH probe

<400> SEQUENCE: 10
tccacttccc tctcccat                                               18
```

METHANE OXIDATION METHODS AND COMPOSITIONS

CROSS REFERENCE TO RELATED APPLICATIONS

This application claims priority to U.S. Provisional Application Ser. No. 62/242,420, filed Oct. 16, 2015, the disclosures of which are incorporated herein by reference.

STATEMENT REGARDING FEDERALLY SPONSORED RESEARCH

This invention was made with Government support under Grant No. DE-SC0010574, DE-SC0004949/T-108572, awarded by the U.S. Department of Energy. The Government has certain rights in the invention.

REFERENCE TO SEQUENCE LISTING

The present application is being filed along with a Sequence Listing in electronic format. The Sequence Listing is provided as a file entitled Sequence_ST25.txt, created Oct. 15, 2016, which is 2146 bytes in size. The information in the electronic format of the Sequence Listing is incorporated herein by reference in its entirety.

TECHNICAL FIELD

Devices and methods to produce electrical energy from methane via $C_1$-metabolizing microorganisms are provided herein.

BACKGROUND

The efficiency in producing electricity from chemical energy (coal, oil, gas, etc.) via mechanical energy (turbines) has a theoretical limit of ca. 60%, which has nearly been reached with combined-cycle gas turbines. The scarceness of energy resources combined with a growing population worldwide will force researchers to find processes that are more efficient. Conversion of fuel to electricity at efficiencies higher than 60% must be "direct", utilizing fuel cell systems that do not go through a step of heat production. For methane, however, direct conversion of methane to electricity in fuel cells is particularly challenging and inefficient. Temperatures of around 650° C. are required to cleave the inert C—H bonds of methane. Moreover, common obstacles such as reaction stability, catalyst poisoning, side reactions and high over potentials must also be overcome. Alternative fuel sources are very much desired both from an economic as well as an environmental stand point. Utilizing sources of possible biological energy to produce biofuel and energy are desirable.

SUMMARY

The disclosure provides devices and methods to produce electrochemical energy from methane via $C_1$-metabolizing microorganisms.

The disclosure provides a bioelectrochemical device comprising a methane source to provide methane to the bioelectrochemical device; an aqueous solvent system that comprises an aqueous soluble electron acceptor that is re-circulated in the bioelectrochemical device; a bioreactor comprising one or more different types of $C_1$-metabolizing microorganisms that are capable of metabolizing methane and reducing the electron acceptor to a reduced electron acceptor; a fuel cell comprising an anode that can oxidize the reduced electron acceptor back to the electron acceptor, a cathode that can reduce an oxidant, and an ion conductor placed between the cathode and anode, wherein the ion conductor selectively transports positively or negatively charged ions. In one embodiment, the bioelectrochemical device further comprises one or more of the following: a series of tubes that are fluidly in contact with the bioreactor and the fuel cell; a pump that powers the recirculation of the solvent system; a check valve that selectively allows the passage of methane into the bioelectrochemical device; a set of valves and inlets that are fluidly in contact with the aqueous solvent system that allow for addition or adjustment of the aqueous solvent system; and/or a $CO_2$ extraction device that removes dissolved $CO_2$ from the aqueous solvent system. In another or further embodiment, the bioelectrochemical device comprises the pump that powers the recirculation of the solvent system; the check valve that selectively allows the passage of methane into the bioelectrochemical device; the set of valves and inlets that are fluidly in contact with the aqueous solvent system that allow for addition or adjustment of the aqueous solvent system; the $CO_2$ extraction device that removes dissolved $CO_2$ from the aqueous solvent system; and/or the series of tubes that are fluidly in contact with the bioreactor, and the fuel cell, wherein the series of tubes are also fluidly in contact with the pump, the check valve, the set of valves and inlets/outlets, and the $CO_2$ extraction device. In still another or further embodiment of any of the foregoing, the one or more different types of $C_1$-metabolizing microorganisms are methanogens, methanotrophs, and/or a recombinantly engineered organism(s) that are capable of oxidizing methane. In yet another embodiment or further embodiment of any of the foregoing, the one or more different types of $C_1$-metabolizing microorganisms are anaerobic methanotrophs; and wherein the aqueous solvent is substantially free or devoid of dissolved oxygen. In still yet another embodiment or further embodiment of any of the foregoing, the methane source is a methane producing fermentation system utilizing biomass, coal, human waste, and/or animal waste as a fuel source, and/or a purified fuel gas stream that is enriched with methane. In yet another embodiment or further embodiment of any of the foregoing the electron acceptor is a single-electron acceptor with a standard reduction potential more positive than ca. −240 mV. In yet a further embodiment, a redox active molecule is used as electron acceptor is selected from the group consisting of 2,6-AQDS (9,10-anthraquinone-2,6-disulfonate), 2,7-AQDS (9,10-anthraquinone-2,7-disulfonate), 1,5-AQDS (9,10-anthraquinone-1,5-disulfonate), Fe(III)-citrate, Fe(III)-EDTA, humic acids, and melanin. In still yet another or further embodiment, the aqueous solvent system further comprises one or more of the following: buffers, salts, and/or nutrients. In another embodiment or further embodiment, the bioreactor comprises: a housing with two surfaces an inner surface that comes into contact with the aqueous solvent and an outer surface that does not come into contact with the aqueous solvent; at least two ports to allow for the aqueous solvent to enter the bioreactor and to allow for the aqueous solvent to exit the bioreactor. In yet a further embodiment, the bioreactor comprises one or more $C_1$-metabolizing microorganisms that are grown or contained within a bed of media or solid support(s). In still yet a further embodiment, the media and solid support comprises a high surface area so that $C_1$-metabolizing microorganisms can spread across the surface of the media or the solid support. In yet another or further embodiment, the solid support is comprised of a porous or very porous material. In still yet another or further embodiment, the bioreactor further comprises filters or membranes that prevent the passage of $C_1$-metabolizing microorganisms or cellular debris out of the bioreactor. In yet another or further embodiment, the aqueous solvent flows into the top of the fuel cell and exits out the bottom of the fuel cell. In still yet another or further embodiment, the aqueous solvent flows into the bottom of the bioreactor and exits out the top of the bioreactor. In still another or further embodiment, the anode and cathode of the fuel cell comprise of electrodes made of carbon or metals such as titanium, and modified by coating with platinum or platinum ruthenium alloys as catalysts; and wherein the ion conductor includes but not limited to a sulfonated tetrafluoroethylene based fluoropolymer-copolymer membrane. In yet another or further embodiment of any of the foregoing, the $CO_2$ extraction device is a membrane degasifier device or $CO_2$-precipitating chemical reactor. In still another or further embodiment of any of the foregoing, wherein the pump, check valve and $CO_2$ extraction device are electronically controlled directly and/or controlled remotely over a network or wireless communication using a computer, cell phone, and/or tablet.

The disclosure also provides a method to produce direct electrical current comprising providing methane to the bioelectrochemical device of the disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the disclosure and, together with the detailed description, serve to explain the principles and implementations of the invention.

FIG. 3A-B Comparison of raw data and calculated concentrations of DIC. Data for two replicate incubations with sulfate-coupled AOM (TABLE 4, incubations "Sulfate [28 mM] A+B") that are used for FIG. 1A and TABLE 2B are shown as examples. (A) Time course of AT % $^{13}C$ measured in DIC. (B) Calculated concentrations of total (black) and newly formed (gray) DIC (see methods). Gray: Calculation used throughout this publication that yields the concentration of newly formed DIC. This method relies on knowing the AT % $^{13}C$ in the methane employed and the initial concentration and isotopic composition of DIC. Black: Independent method via standard addition that directly yields the absolute concentration of DIC for any time point. This method was employed to provide evidence for net DIC increase during incubations. This method does not account for the inorganic carbon present as gaseous $CO_2$ in the headspace.

FIG. 7A-F displays representative FISH-nanoSIMS images from sulfate and AQDS microcosms. The correlation between phylogenetic identity (FISH) and anabolic activity ($^{15}N$ enrichment) for example consortia of ANME-2c archaea and sulfate-reducing bacteria analyzed from AOM incubations amended with sulfate or AQDS is shown. (A-C) AOM consortium from microcosm with sulfate. (D-F) Consortium from microcosm with AQDS as the sole electron acceptor. In each case, the at % of $^{15}N$ isotope enrichment was calculated from ratios of secondary ion images of $^{12}C^{15}N^{1-}$ and $^{12}C^{14}N^{1-}$. (A) and (D) FISH images, with ANME-2c in dark gray and Desulfobacteraceae in light gray; the FISH signal for the bacterial cells in (D) is weak, probably due to the low abundance of cellular rRNA in SRB in the AQDS treatment without sulfate. (B) and (E) nanoSIMS ion image of $^{12}C^{14}N^{1-}$ for cellular biomass, linear scale (0 to 4500 counts per pixel). (C) and (F) Fractional abundance of $^{15}N$ (in at %) as a proxy for anabolic activity.

FIG. 8A-B provides a summary of FISH-nanoSIMS $^{15}N$ incorporation data. Average anabolic activity for paired ANME and SRB populations in each AOM consortium from incubations with different terminal electron experiments is shown. Each solid symbol represents the average $^{15}N$ at % for the population of paired ANME-2c cells relative to bacterial cells in a single consortium. Open symbols represent other unidentified ANME-SRB consortia (putative ANME-2a). (Insets) $^{15}N$ at % values close to natural abundance value (0.36 at % $^{15}N$). FISH-nanoSIMS images of consortia marked with an arrow are displayed in FIG. 7 and FIGS. 9 and 10. (A) and (B) constitute two independent sets of experiments; experiments in (A) contained ~80%

Figure 1A:
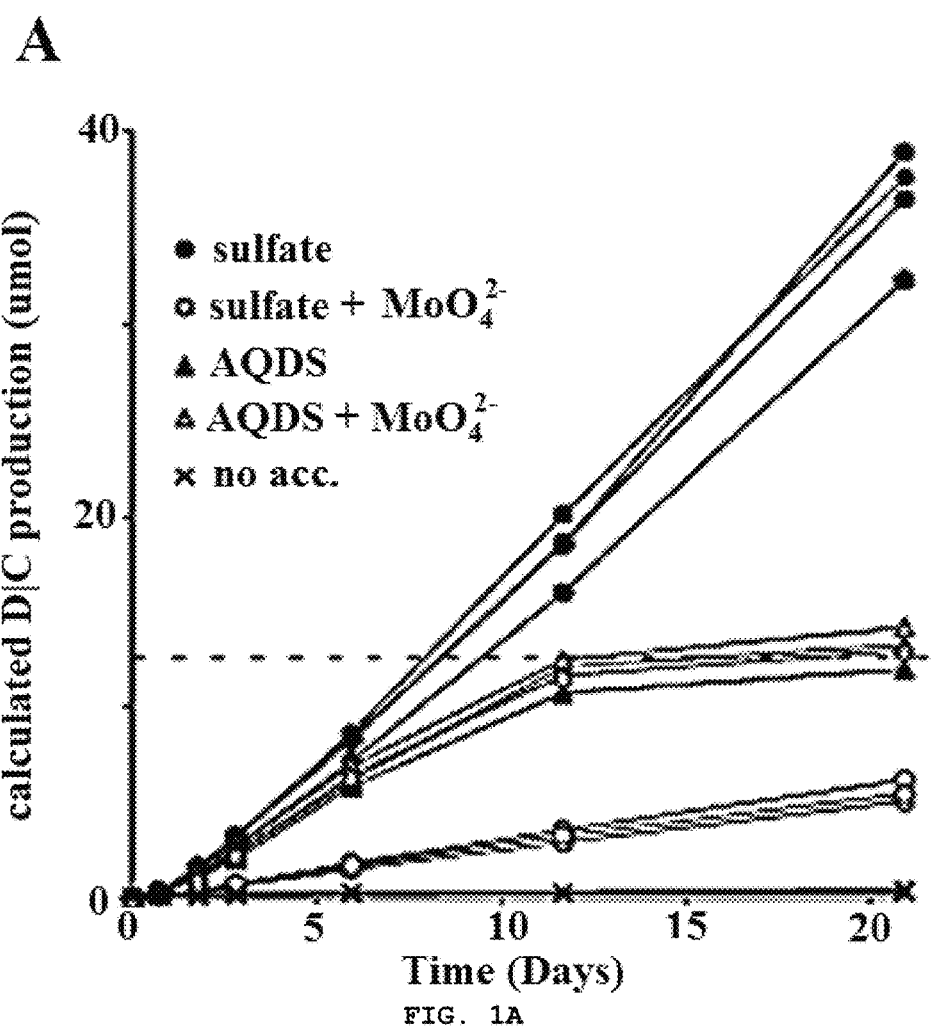
FIG. 1A-B provides the dissolved inorganic carbon (DIC) production per vial in incubations with 1.0 cm³ of a methane seep sediment. (A) Methane oxidation coupled to sulfate reduction [140 mmol of $SO_4^{2-}$ (28 mM), methane oxidation unlimited, circles], and methane oxidation coupled to AQDS reduction [50 mmol of AQDS (10 mM) in the absence of sulfate, triangles]. Due to the 1:4 stoichiometry between $CH_4$ and AQDS, the produced DIC plateaued at approximately 12.5 mmol (dashed line). Open symbols depict incubations with the addition of the sulfate-reduction inhibitor sodium molybdate (25 mM). Control incubations without electron acceptors added (x symbol). (B) Initial rates of methane oxidation with different electron acceptors for individual incubation bottles. Values from the linear regression of time points 1 to 6 days (four points) are calculated per cubic centimeter of wet sediment; error bars represent the 95% confidence interval. White bars depict incubations with sodium molybdate (25 mM). Time course measurements for these experiments are provided in FIG. 2; raw data are provided in FIG. 3.

$^{15}NH_4^+$, whereas those in (B) contained ~40%. The activity of bacterial cells (b) relative to the archaeal cell activity (a) was determined via linear regression as follows: (A) Sulfate: b=0.97a+2.17, R2=0.75; AQDS: b=0.070a+0.39, R2=0.69. (B) Sulfate: b=1.09a+1.07, R2=0.74; iron citrate: b=0.28a+ 0.25, R2=0.71; humic acids: b=0.21a+0.29, R2=0.60. The darker gray data point in parentheses (A) was not included for the linear regression (see FIG. 11 for single-cell analysis and further discussion). The small apparent $^{15}N$ enrichment in bacteria from sulfate-free incubations was found to be due to inaccuracies in pixel assignments for SRB cells during data processing, determined by manual inspection of each nanoSIMS image.

FIG. 9A-I provides FISH-nanoSIMS analysis of consortia incubated with different oxidants or electron acceptor. Representative consortia recovered from a second set of experiments with PC61 (see FIG. 8B) incubated with ferric citrate, humic acids, or sulfate. (A-C), With sulfate; (D-F), with ferric citrate in the presence of the sulfate-reducing inhibitor sodium molybdate (25 mM); (G-I), with humic acids as the oxidant or electron acceptor. (A, D, G) FISH images, ANME-2c (in medium gray), Desulfobacteraceae (in light gray); (A) DAPI image (in darker gray) included. Scale bar=5 μm for all FISH images. (B, E, H) nanoSIMS ion image of $^{12}C^{14}N^{1-}$ showing cell biomass, linear scale. (C, F, I) fractional abundance of $^{15}N$ (in AT %) measured by nanoSIMS as a proxy for newly synthesized biomass. Here, the minimum value on the scale was set to 0.3 AT % (black), close to the natural abundance $^{15}N$ (0.36 AT %).

FIG. 10A-C provides an example of FISH-nanoSIMS of the consortium incubated without an oxidant or electron acceptor. ANME-2c/DSS consortium recovered from the microcosm treatment supplied with a methane headspace but no added electron acceptor. Data was acquired after 18 days of incubation in the presence of $^{15}NH_4^+$ (see FIG. 7A, inset). (A) FISH images, ANME-2c (in dark gray), Desulfobacteraceae (in light gray). (B) NanoSIMS ion image of $^{12}C^{14}N^{1-}$ showing cell biomass, linear scale. (C) Fractional abundance of $^{15}N$ (in AT %) as a proxy for newly synthesized biomass.

FIG. 11A-C presents FISH-nanoSIMS data from the outlier ANME-2c consortium. This consortium was excluded from the activity correlation (see FIG. 8A)*. (A) FISH images, ANME-2c (in medium gray), Desulfobacteraceae, DSS (in light gray), DAPI (in dark gray). (B) NanoSIMS ion image of $^{12}C^{14}N^{1-}$ showing cell biomass, linear scale. (C) Fractional abundance of $^{15}N$ (in AT %) as a proxy for newly synthesized biomass. * The low ratio of bacterial/archaeal $^{15}N$ incorporation (ratio=0.386) for incubations with sulfate is represents an outlier from all other analyzed consortia from this treatment as well as our previously published FISH-nanoSIMS experiments. For this reason, ANME-2c aggregate (with an unidentified bacterial partner) was excluded from the linear regression of the overall activities displayed in FIG. 8A.

FIG. 12 provides a Table of nanoSIMS $^{15}N$ and $^{14}N$ total ion counts. Calculation of $^{15}N$ fractional abundance (anabolic activity proxy) for paired archaea (a) and bacteria (b) in consortia from all 6 incubation conditions supplied with $^{15}NH_4^+$.

Figure 13:
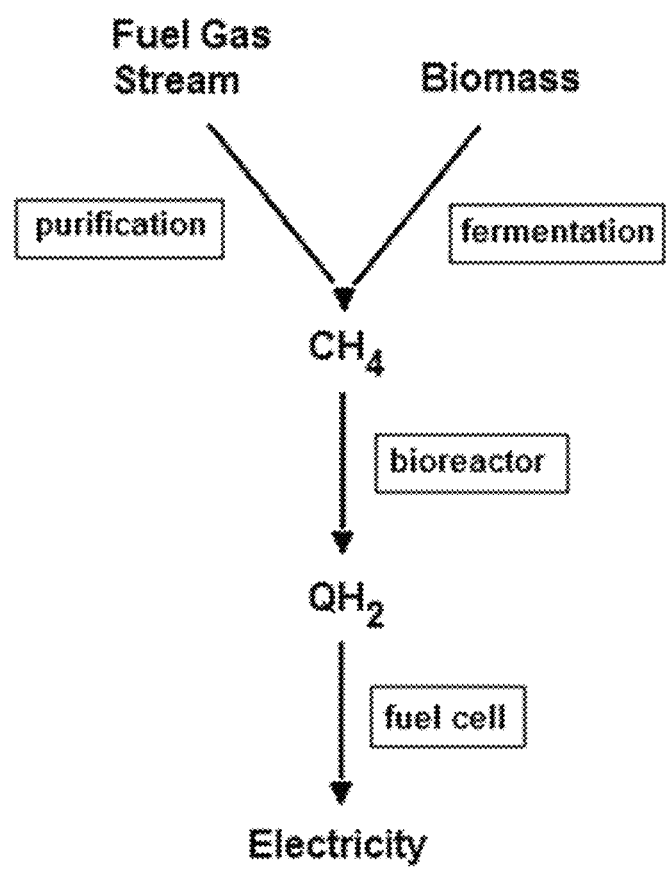

FIG. 13 provides a flow chart of an embodiment of an overall process which can be used to convert methane from methane sources (e.g., fuel gas stream or biomass) to electrochemical energy using the bioelectrochemical device of the disclosure.

Figure 14:
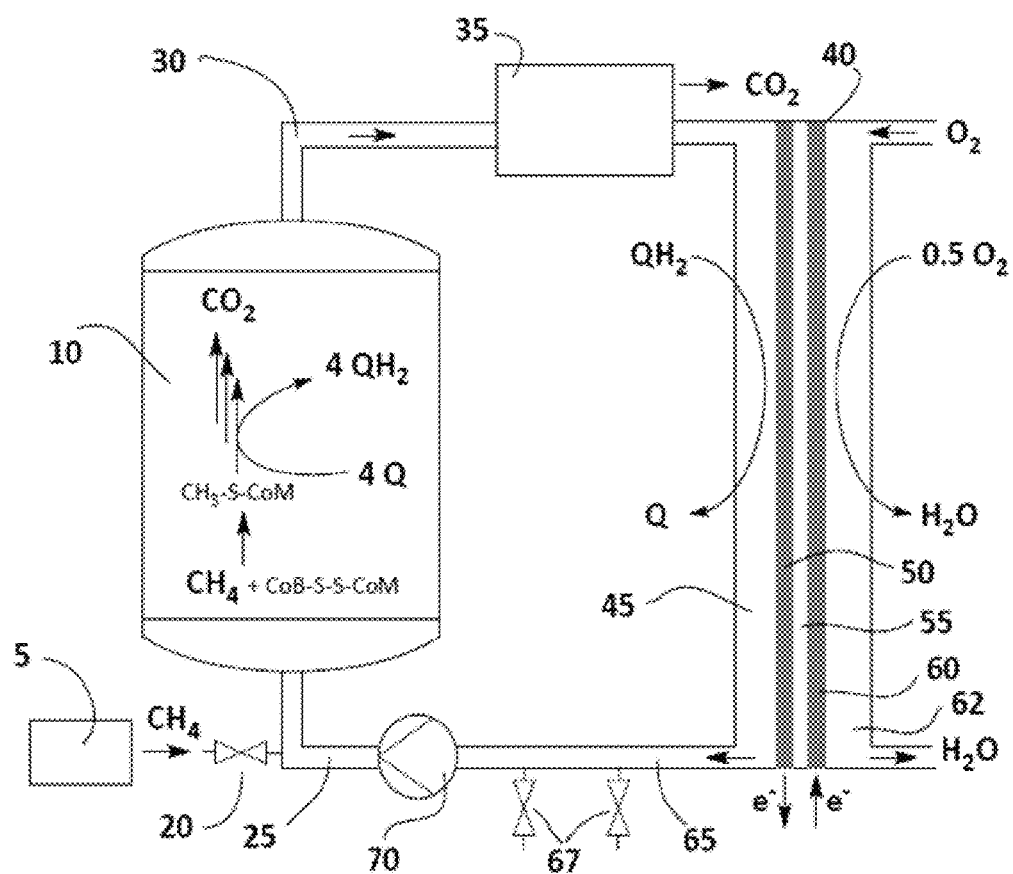

FIG. 14 provides an exemplary bioelectrochemical device of the disclosure which comprises a bioreactor with internal cycling of an electron acceptor (Q).

Figure 15:
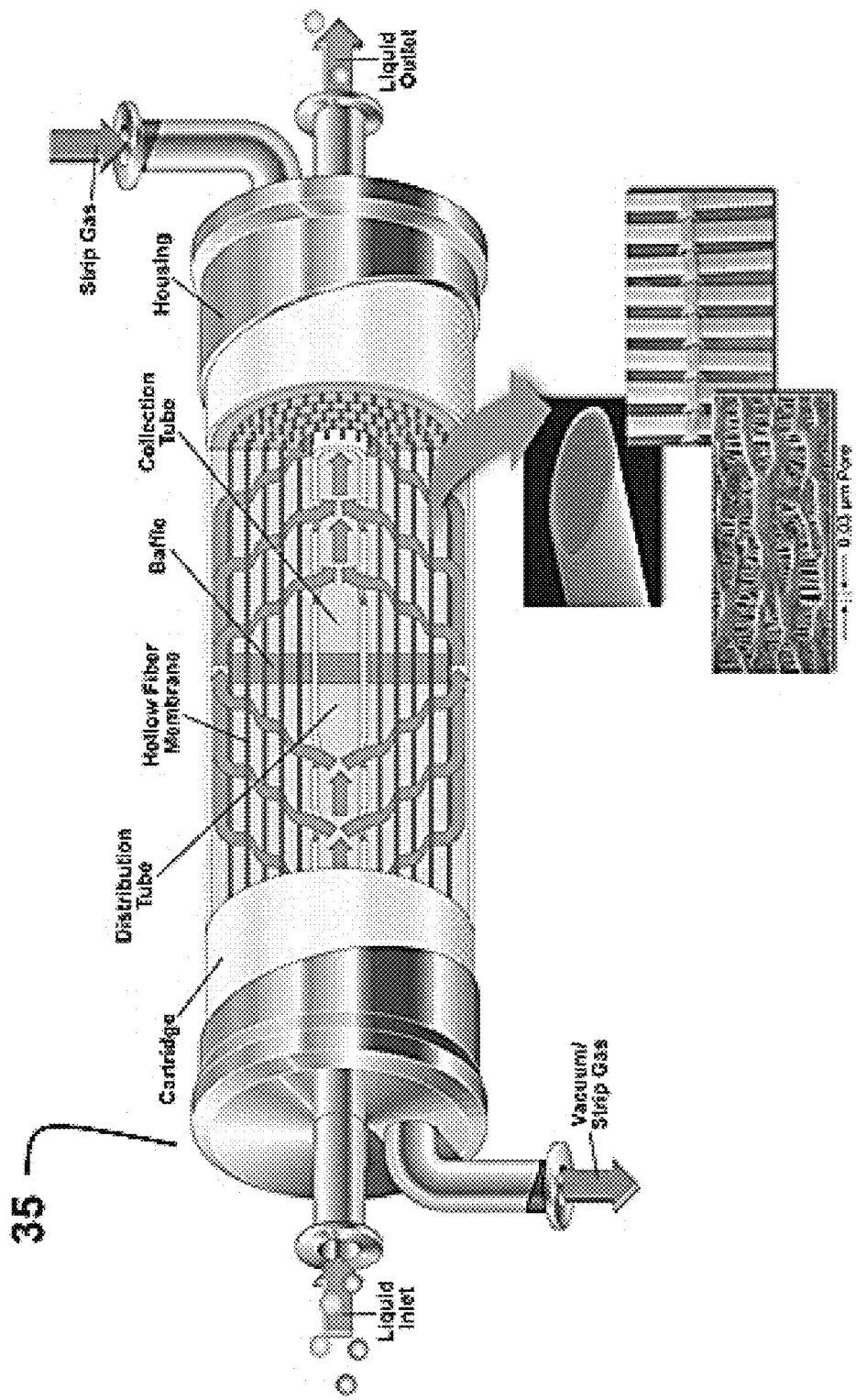

FIG. 15 provides an exemplary membrane degasifier that can be used with a bioelectrochemical device of the disclosure.

DETAILED DESCRIPTION

As used herein and in the appended claims, the singular forms "a," "an," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

As used herein, the terms "$C_1$-metabolizing microorganism" or "$C_1$-metabolizing non-photosynthetic microorganism" refers to any microorganism having the ability to use a $C_1$-substrate as a source of energy or as its sole source of energy and biomass, and may or may not use other carbon substrates (such as sugars and complex carbohydrates) for energy and biomass. For example, a $C_1$-metabolizing microorganism may oxidize a $C_1$ substrate, such as methane, and methanol. $C_1$-metabolizing microorganisms include Bacteria (such as aerobic methanotrophs in the phylum of Proteobacteria or Verrucomicrobia) and Archaea (such as methanogens and anaerobic methanotrophs in the phylum of Euryarchaeota and orders of Methanobacteriales, Methanococcales, Methanomicrobiales, Methanosarcinales, Methanocellales, Methanopyrales and Methanomassiliicoccales, or potentially in the phylum of Bathyarchaeota or Verstraetearchaeota) and yeast. In at least some instances, a $C_1$-metabolizing microorganism does not include a photosynthetic microorganism, such as algae. In certain embodiments, the $C_1$-metabolizing microorganism could be an "obligate methane metabolizing microorganism," meaning its sole source of energy comprises methane and nothing else.

As used herein, the term "methylotrophic organism" refers to any organism capable of oxidizing organic compounds that do not contain carbon-carbon bonds. In certain embodiments, a methylotrophic organism may be a methanotroph. For example, "methanotrophic organism" refers to any methylotrophic organism that has the ability to oxidize methane as its primary source of carbon and energy. Exemplary methanotrophic organisms include, but are not limited to, *Methylomonas, Methylobacter, Methylococcus, Methylo-*

*sinus, Methylocystis, Methylomicrobium,* or *Methanomonas* in the Domain of Bacteria, and those in phylum of Euryarchaeota such as Anaerobic Methanotrophic Archaea (ANME) clade 1, 2 or 3 (or ANME-1, ANME-2, ANME-3 respectively), Methanoperedens (formerly known as ANME-2d), or in the phylum of Bathyarchaeota or Verstraetearchaeota in the Domain of Archaea. In certain other embodiments, the methylotrophic organism is an "obligate methylotrophic organism," which refers to organisms that are limited to the use of $C_1$ substrates for the generation of energy.

The term "microorganism" includes archaeal, bacterial and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "prokaryotes" is art recognized and refers to cells which contain no nucleus or other cell organelles. The prokaryotes generally refer to two of three Domains of life, namely the Bacteria and the Archaea. The definitive difference between organisms of the Archaea and Bacteria domains is based on fundamental differences in the nucleotide base sequence in the 16S ribosomal RNA gene.

The term "Archaea" refers to a categorization of organisms formerly of the division Mendosicutes, typically found in unusual environments and distinguished from the rest of the prokaryotes by several criteria, including the number of ribosomal proteins and the lack of muramic acid in cell walls. On the basis of 16s rRNA analysis, the Archaea consist of multiple phylogenetically-distinct groups, including but not limited to Euryarchaeota, Bathyarchaeota, Verstraetearchaeota and Crenarchaeota. Besides the unifying archaeal features that distinguish them from Bacteria (i.e., no murein in cell wall, ester-linked membrane lipids, etc.), these prokaryotes exhibit unique structural or biochemical attributes which adapt them to their particular habitats.

"Bacteria", or "eubacteria", refers to one of three Domains of life. Bacteria include at least 74 distinct phylums widely distributed in the environment with a range of metabolisms.

As used herein, an "activity" of an enzyme is a measure of its ability to catalyze a reaction resulting in a metabolite, i.e., to "function", and may be expressed as the rate at which the metabolite of the reaction is produced. For example, enzyme activity can be represented as the amount of metabolite produced per unit of time or per unit of enzyme (e.g., concentration or weight), or in terms of affinity or dissociation constants.

The term "biosynthetic pathway", also referred to as "metabolic pathway", refers to a set of anabolic or catabolic biochemical reactions for converting (transmuting) one chemical species into another. Gene products (e.g., enzymes or polypeptides) belong to the same "metabolic pathway" if they, in parallel or in series, act on the same substrate, produce the same product, or act on or produce a metabolic intermediate (i.e., metabolite) between the same substrate and metabolite end product. The disclosure provides recombinant microorganism having a metabolically engineered pathway for the production of a desired product or intermediate.

Accordingly, metabolically "engineered" or "modified" microorganisms are produced via the introduction of genetic material into a host or parental microorganism of choice thereby modifying or altering the cellular physiology and biochemistry of the microorganism. Through the introduction of genetic material, the parental microorganism acquires new properties, e.g. the ability to produce or consume a new, or greater quantities of, an intracellular metabolite. In an illustrative embodiment, the introduction of genetic material into a parental microorganism results in a new or modified ability to metabolize methane or methanol. The genetic material introduced into the parental microorganism contains gene(s), or parts of gene(s), coding for one or more of the enzymes involved in a biosynthetic pathway for the production or consumption of formylmethanofuran, 5-formyl-5,6,7,8-tetrahydromethanopterin, 5,10-methenyltetrahydromethanopterin, 5,10-methylenetetrahydromethanopterin, 5-methyltetrahydromethanopterin, methylcoenzyme M, coenzyme M 7-mercaptoheptanoylthreonine-phosphate heterodisulfide, acetyl phosphate, acetyl coenzyme A, and may also include additional elements for the expression and/or regulation of expression of these genes into functional enzyme products, e.g. promoter sequences, chaperones, post-translational modification enzymes, and cofactor and coenzyme synthesis and incooperation pathways and enzymes.

An "enzyme" means any substance, typically composed wholly or largely of amino acids making up a protein or polypeptide with possibly post-translational modifications that catalyzes or promotes, more or less specifically, one or more chemical or biochemical reactions.

A "protein" or "polypeptide", which terms are used interchangeably herein, comprises one or more chains of chemical building blocks called amino acids that are linked together by chemical bonds called peptide bonds, and may include cofactors as well as post-translational modifications for their intended function and catalysis. A protein or polypeptide can function as an enzyme.

As used herein, the term "metabolically engineered" or "metabolic engineering" involves rational pathway design and assembly of polypeptides having a desired activity, biosynthetic genes, genes associated with operons, and/or control elements of such polynucleotides, for the production of a desired metabolite, such as an formylmethanofuran, 5-formyl-5,6,7,8-tetrahydromethanopterin, 5,10-methenyltetrahydromethanopterin, 5,10-methylenetetrahydromethanopterin, 5-methyltetrahydromethanopterin, methylcoenzyme M, coenzyme M 7-mercaptoheptanoylthreonine-phosphate heterodisulfide, acetyl phosphate, acetyl coenzyme A, higher alcohols or other chemical, in vitro or in a microorganism. "Metabolically engineered" can further include optimization of metabolic flux, particular reaction conditions, optimization of transcription, translation, protein stability and protein functionality using genetic engineering and appropriate culture condition including the reduction of, disruption, or knocking out of, a competing metabolic pathway that competes with an intermediate leading to a desired pathway. A biosynthetic gene can be heterologous to the host microorganism, either by virtue of being foreign to the host, or being modified by mutagenesis, recombination, and/or association with a heterologous expression control sequence in an endogenous host cell. In one embodiment, where the polynucleotide is xenogenetic to the host organism, the polynucleotide can be codon optimized.

A "metabolite" refers to any substance produced by metabolism or a substance necessary for or taking part in a particular metabolic process that gives rise to a desired metabolite, chemical, alcohol or ketone. A metabolite can be an organic compound that is a starting material (e.g., methanol, methane, formaldehyde etc.), an intermediate in (e.g., formic acid), or an end product (e.g., carbon dioxide or dissolved inorganic carbon) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

A "native" or "wild-type" protein, enzyme, polynucleotide, gene, or cell, means a protein, enzyme, polynucleotide, gene, or cell that occurs in nature.

A "parental microorganism" refers to a cell used to generate a recombinant microorganism. The term "parental microorganism" describes, in one embodiment, a cell that occurs in nature, i.e., a "wild-type" cell that has not been genetically modified. The term "parental microorganism" further describes a cell that serves as the "parent" for further engineering. In this latter embodiment, the cell may have been genetically engineered, but serves as a source for further genetic engineering.

For example, a wild-type microorganism can be genetically modified to express or over express a first target enzyme such as a methyl-coenzyme M reductase. This microorganism can act as a parental microorganism in the generation of a microorganism modified to express or over-express a second target enzyme, e.g., a methyltetrahydromethanopterin:coenzyme M methyl-transferase. In turn, that microorganism can be modified to express or over express a third target enzyme, e.g., a heterodisulphide reductase. As used herein, "express" or "over-express" refers to the phenotypic expression of a desired gene product. In one embodiment, a naturally occurring gene in the organism can be engineered such that it is linked to a heterologous promoter or regulatory domain, wherein the regulatory domain causes expression of the gene, thereby modifying its normal expression relative to the wild-type organism. Alternatively, the organism can be engineered to remove or reduce a repressor function on the gene, thereby modifying its expression. In yet another embodiment, a cassette comprising the gene sequence operably linked to a desired expression control/regulatory element is engineered in to the microorganism.

Accordingly, a parental microorganism functions as a reference cell for successive genetic modification events. Each modification event can be accomplished by introducing one or more nucleic acid molecules into the reference cell. The introduction facilitates the expression or over-expression of one or more target enzyme or the reduction or elimination of one or more target enzymes. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of exogenous polynucleotides encoding a target enzyme into a parental microorganism.

Polynucleotides that encode enzymes useful for generating metabolites (e.g., enzymes such as methyl-coenzyme M reductase, methyltetrahydromethanopterin: coenzyme M methyl-transferase, heterodisulphide reductase, F420-dependent methylenetetrahydromethanopterin reductase, F420-dependent methylenetetrahydromethanopterin dehydrogenase, methenyltetrahydromethanopterin cyclohydrolase, formylmethanofuran: tetrahydromethanopterin formyltransferase, formylmethanofuran dehydrogenase, ATP: acetate phosphotransferase, acetyl-CoA: phosphate acetyltransferase, acetate: CoA ligaseacetyl-CoA decarbonylase/synthase) including homologs, variants, fragments, related fusion proteins, or functional equivalents thereof, are used in recombinant nucleic acid molecules that direct the expression of such polypeptides in appropriate host cells, such as prokaryotic or eukaryotic cells.

Exemplary protein sequences encoded by polynucleotides can be found below from published genomes of methanogenic archaea and published incomplete genomes of methanotrophic archaea. These genes and their homologs are useful in the methods described herein, include but are not limited to the following listed in Table 1:

TABLE 1

Examples of protein sequences encoded by polypeptides from two methanogenic archaea.

| Gene | Full_Name | Methanosarcina barkeri str. Fusaro | Methanococcus maripaludis X1 |
|---|---|---|---|
| fmdA | formylmethanofuran dehydrogenase subunit A | WP_011306299 | WP_011170453 |
| fmdB | formylmethanofuran dehydrogenase subunit B | WP_011306302 | WP_013999131 |
| fmdC | formylmethanofuran dehydrogenase subunit C | WP_011306300 | WP_013999132 |
| fmdD | formylmethanofuran dehydrogenase subunit D | WP_011306301 | AEK19995 |
| fmdE | formylmethanofuran dehydrogenase subunit E | WP_011306297 | WP_013999133 |
| fmdF | formylmethanofuran dehydrogenase subunit F | AAZ71499 | AEK20270 |
| fmdG | formylmethanofuran dehydrogenase subunit G | AAZ71816 | |
| fmdH | formylmethanofuran dehydrogenase subunit H | | AEK20269 |
| ftr | formylmethanofuran-- tetrahydromethanopterin N-formyltransferase | WP_011306001 | WP_013999908 |
| mch | methenyltetrahydromethan- opterin cyclohydrolase | WP_011307204 | WP_013999597 |
| mtd | methylenetetrahydromethan- opterin dehydrogenase | WP_011306111 | WP_011171660 |
| mer | 5,10- methylenetetrahydromethan- opterin reductase | WP_011305293 | WP_013998544 |

TABLE 1-continued

| Gene | | | |
|---|---|---|---|
| mtrA | tetrahydromethanopterin S-methyltransferase subunit A | WP_011306268 | WP_013999872 |
| mtrB | tetrahydromethanopterin S-methyltransferase subunit B | WP_011306269 | WP_011171507 |
| mtrC | tetrahydromethanopterin S-methyltransferase subunit C | WP_011306270 | WP_011171506 |
| mtrD | tetrahydromethanopterin S-methyltransferase subunit D | WP_011306271 | WP_011171505 |
| mtrE | tetrahydromethanopterin S-methyltransferase subunit E | WP_011306272 | WP_013999871 |
| mtrF | tetrahydromethanopterin S-methyltransferase subunit F | WP_011306267 | |
| mtrG | tetrahydromethanopterin S-methyltransferase subunit G | WP_011306266 | WP_011171510 |
| mtrH | tetrahydromethanopterin S-methyltransferase subunit H | WP_011306265 | WP_011171511 |
| mcrA | methyl-coenzyme M reductase subunit A | WP_011305916 | WP_013999870 |
| mcrB | methyl-coenzyme M reductase subunit B | WP_011305920 | WP_011171499 |
| mcrC | methyl-coenzyme M reductase subunit C | WP_011305918 | WP_011171501 |
| mcrD | methyl-coenzyme M reductase subunit D | WP_011305919 | WP_013999868 |
| mcrG | methyl-coenzyme M reductase subunit G | WP_011305917 | WP_013999869 |
| hdrA | heterodisulfide reductase subunit A | AAZ71500 | AEK19828 |
| hdrB | heterodisulfide reductase subunit B | AAZ70892 | WP_013999494 |
| hdrC | heterodisulfide reductase subunit C | AAZ70891 | WP_013999495 |
| hdrD | heterodisulfide reductase subunit D | P96797.4 | |
| hdrE | heterodisulfide reductase subunit E | P96796.2 | |
| mtaA | [methyl-Co (III) methanol-specific corrinoid protein]: coenzyme M methyltransferase | Q48949 | |
| mtaB | methanol---5-hydroxybenzimidazolyl-cobamide Co-methyltransferase | Q46EH3 | |
| mtaC | methanol corrinoid protein | AAZ72501 | |

Examples of protein sequences encoded by polypeptides from archaea involved in or potentially involved in anaerobic oxidation of methane.

| Gene | ANME-1 (Meyerdierks et al. 2010) | ANME-2a (Wang et al. 2014) | Candidatus Methanoperedens nitroreducens (Haroon al. et 2013) | Candidatus Bathyarchaeota archaeon BA1 (Evans et al. 2015) | Candidatus Bathyarchaeota archaeon BA2 (Evans et al. 2015) |
|---|---|---|---|---|---|
| fmdA | CBH38674 | IMG 2566126780 | KCZ72275 | | |
| fmdB | CBH38673 | IMG 2566124824 | KCZ72274 | | |
| fmdC | CBH38675 | IMG 2566125475 | KCZ72276 | KPV62166 | |
| fmdD | CBH38672 | IMG 2566124823 | KCZ72273 | | |
| fmdE | | IMG 2566125238 | KCZ73342 | | |
| fmdF | | IMG 2566123321 | | | |

TABLE 1-continued

| | | | | | |
|---|---|---|---|---|---|
| fmdG | | IMG 2566125853 | | | |
| fmdH | | | | | |
| ftr | CBH38579 | IMG 2566123292 | KCZ73568 | KPV63694 | KPV63869 |
| mch | CBH37751 | IMG 2566124083 | KCZ70764 | KPV62158 | |
| mtd | CBH37899 | IMG 2566126853 | | | |
| mer | | IMG 2566123633 | KCZ71526 | KPV65334 | |
| mtrA | CBH38255 | IMG 2566123987 | KCZ73426 | | |
| mtrB | CBH38256 | IMG 2566123988 | KCZ73425 | | |
| mtrC | CBH38257 | IMG 2566123989 | KCZ73424 | | |
| mtrD | CBH38258 | IMG 2566123990 | KCZ73423 | | |
| mtrE | CBH38259 | IMG 2566123991 | KCZ73422 | | |
| mtrF | | | KCZ73427 | | |
| mtrG | CBH38253 | IMG 2566125855 | KCZ73428 | | |
| mtrH | CBH38252 | IMG 2566123984 | KCZ71022 | KPV64965 | |
| mcrA | CBH37407 | IMG 2566125579 | KCZ72673 | KPV65186 | KPV61791 |
| mcrB | CBH37405 | IMG 2566125583 | KCZ72670 | KPV65184 | KPV61799 |
| mcrC | CBH37386 | IMG 2566125581 | KCZ72448 | | KPV61780 |
| mcrD | | IMG 2566125582 | KCZ72671 | | KPV61779 |
| mcrG | CBH37406 | IMG 2566125580 | KCZ72672 | KPV65185 | KPV61800 |
| hdrA | CBH38803 | IMG 2566125169 | KCZ70533 | KPV63203 | KPV64464 |
| hdrB | CBH38352 | IMG 2566124428 | KCZ71427 | KPV63202 | KPV61761 |
| hdrC | CBH37748 | IMG 2566124427 | KCZ71093 | KPV63201 | KPV61762 |
| hdrD | | IMG 2566126466 | | KPV65052 | KPV63063 |
| hdrE | | IMG 2566126467 | KCZ70770 | | |

It is understood that the addition of sequences which do not alter the encoded activity of a nucleic acid molecule, such as the addition of a non-functional or non-coding sequence (e.g., poly HIS tags), is a conservative variation of the basic nucleic acid.

In addition to methane metabolizing genes, methanotrophic archaea or engineered host should contain a mechanism to interact with extracellular electron acceptors and transfer electrons to these redox active molecules. Potential proteins found in ANME-2 such as ANME-2a (IMG Gene ID 2566123487 and 2566125052), ANME-2b (NCBI Accession Number KR811028), ANME-2d or Methanoperedens nitroreducens (IMG Gene ID 2515322983, 2515320866) together with membrane and extracellular cytochrome b and/or c such as the one in ANME-2a (IMG Gene ID 2566125773 and 2566125774) and their homologs, as well as promoter sequences, chaperons and genes associated with their synthesis and operation with the reverse methanogenesis or methane oxidation genes list in Table 1 are useful in the methods described herein and represent one way to transfer electrons to electron acceptors. Other ways of transferring electrons to extracellular electron acceptors include but not limited to the systems described in bacterial genuses Geobacter, Shewanella, and Rhodopseudomonas involving genes omcB (NCBI Accession Number WP_010943369), cytochrome C (NCBI Accession Number AJY69163), ppcA (NCBI Accession Number AAN40982), mtrA (NCBI Accession Number NP_717386), mtrB (NCBI Accession Number NP_717385), mcrC (NCBI Accession Number NP_717387), cymA (NCBI Accession Number NP_720107.1), pioA (NCBI Accession Number ABL63052), pioB (NCBI Accession Number ABL63053), pioC (NCBI Accession Number ABL63054) and their homologs, as well as promoter sequences, chaperons and genes associated with their synthesis and operation with the reverse methanogenesis or methane oxidation genes list in Table 1.

It is understood that a polynucleotide described herein include "genes" and that the nucleic acid molecules described above include "vectors" or "plasmids." For example, a polynucleotide encoding a methyl-coenzyme M reductase can comprise an mcrA gene or homolog thereof, or an mcrB gene or homolog thereof, or a mcrG gene or homolog thereof. Accordingly, the term "gene", also called a "structural gene" refers to a polynucleotide that codes for a particular polypeptide comprising a sequence of amino acids, which comprise all or part of one or more proteins or enzymes, and may include regulatory (non-transcribed) DNA sequences, such as promoter region or expression control elements, which determine, for example, the conditions under which the gene is expressed, in cooperation with cofactors such as Fe or Ni, synthesis and in cooperation with coenzymes such as heme or iron-sulfur clusters, as well as addition of post-translational modifications. The transcribed region of the gene may include untranslated regions, including introns, 5'-untranslated region (UTR), and 3'-UTR, as well as the coding sequence.

The term "polynucleotide," "nucleic acid" or "recombinant nucleic acid" refers to polynucleotides such as deoxyribonucleic acid (DNA), and, where appropriate, ribonucleic acid (RNA).

The term "expression" with respect to a gene or polynucleotide refers to transcription of the gene or polynucleotide and, as appropriate, translation of the resulting mRNA transcript to a protein or polypeptide. Thus, as will be clear from the context, expression of a protein or polypeptide results from transcription and translation of the open reading frame.

Those of skill in the art will recognize that, due to the degenerate nature of the genetic code, a variety of codons differing in their nucleotide sequences can be used to encode a given amino acid. A particular polynucleotide or gene sequence encoding a biosynthetic enzyme or polypeptide described above are referenced herein merely to illustrate an embodiment of the disclosure, and the disclosure includes polynucleotides of any sequence that encode a polypeptide comprising the same amino acid sequence of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with alternate amino acid sequences, and the amino acid sequences encoded by the DNA sequences shown herein merely illustrate exemplary embodiments of the disclosure.

The disclosure provides polynucleotides in the form of recombinant DNA expression vectors or plasmids, as described in more detail elsewhere herein, that encode one or more target enzymes. Generally, such vectors can either replicate in the cytoplasm of the host microorganism or integrate into the chromosomal DNA of the host microorganism. In either case, the vector can be a stable vector (i.e., the vector remains present over many cell divisions, even if only with selective pressure) or a transient vector (i.e., the vector is gradually lost by host microorganisms with increasing numbers of cell divisions). The disclosure provides DNA molecules in isolated (i.e., not necessarily pure, but existing in a preparation in an abundance and/or concentration not found in nature) and purified (i.e., substantially free of contaminating materials or substantially free of materials with which the corresponding DNA would be found in nature) form.

A polynucleotide of the disclosure can be amplified using cDNA, mRNA or alternatively, genomic DNA, as a template and appropriate oligonucleotide primers according to standard PCR amplification techniques and those procedures described in the Examples section below. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer.

It is also understood that an isolated polynucleotide molecule encoding a polypeptide homologous to the enzymes described herein can be created by introducing one or more nucleotide substitutions, additions or deletions into the nucleotide sequence encoding the particular polypeptide, such that one or more amino acid substitutions, additions or deletions are introduced into the encoded protein. Mutations can be introduced into the polynucleotide by standard techniques, such as site-directed mutagenesis and PCR-mediated mutagenesis. In contrast to those positions where it may be desirable to make a non-conservative amino acid substitution, in some positions it is preferable to make conservative amino acid substitutions.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

The term "recombinant microorganism" and "recombinant host cell" are used interchangeably herein and refer to microorganisms that have been genetically modified to express or over-express endogenous polynucleotides, or to express non-endogenous sequences, such as those included in a vector. The polynucleotide generally encodes a target enzyme involved in a metabolic pathway for producing a desired metabolite as described above, but may also include protein factors necessary for regulation or activity or transcription. Accordingly, recombinant microorganisms described herein have been genetically engineered to express or over-express target enzymes not previously expressed or over-expressed by a parental microorganism. It is understood that the terms "recombinant microorganism" and "recombinant host cell" refer not only to the particular recombinant microorganism but to the progeny or potential progeny of such a microorganism.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, but also intermediate and end product metabolites used in a pathway associated with a metabolically engineered microorganism as described herein.

"Transformation" refers to the process by which a vector is introduced into a host cell. Transformation (or transduction, or transfection), can be achieved by any one of a number of means including electroporation, microinjection, biolistics (or particle bombardment-mediated delivery), or *agrobacterium* mediated transformation.

A "vector" generally refers to a polynucleotide that can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, *Streptomyces*, and other cells including archaea that have been published in the literature and/or are available commercially. For example, suitable promoters for inclusion in the expression vectors of the disclosure include those that function in eukaryotic or prokaryotic host microorganisms. Promoters can comprise regulatory sequences that allow for regulation of expression relative to the growth of the host microorganism or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433, which is incorporated herein by reference in its entirety), can also be used. For expression vectors such as those been demonstrated in *E. coli*, it is useful to include an *E. coli* origin of replication, such as from pUC, pIP, p1, and pBR.

Thus, recombinant expression vectors contain at least one expression system, which, in turn, is composed of at least a portion of a gene coding sequences operably linked to a promoter and optionally termination sequences that operate to effect expression of the coding sequence in compatible host cells. The host cells are modified by transformation with the recombinant DNA expression vectors of the disclosure to contain the expression system sequences either as extrachromosomal elements or integrated into the chromosome.

In addition, and as mentioned above, homologs of enzymes useful for generating metabolites are encompassed by the microorganisms and methods provided herein. The term "homologs" used with respect to an original enzyme or gene of a first family or species refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson et al., 1994, hereby incorporated herein by reference).

In some instances, "isozymes" can be used that carry out the same functional conversion/reaction, but which are so dissimilar in structure that they are typically determined to not be "homologous".

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which can also be referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A typical algorithm used to compare a target sequence to a database containing a large number of sequences from different organisms is the computer program BLAST (Altschul, 1990; Gish, 1993; Madden, 1996; Altschul, 1997; Zhang, 1997), especially blastp or tblastn (Altschul, 1997). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, hereby incorporated herein by reference). For example, percent sequence identity between amino acid sequences can be determined using FASTA with its default parameters (a word size of 2 and the PAM250 scoring matrix), as provided in GCG Version 6.1, hereby incorporated herein by reference.

The disclosure provides accession numbers for various genes, homologs and variants useful in the generation of synthetic pathways and/or recombinant microorganism described herein. It is to be understood that homologs and variants described herein are exemplary and non-limiting. Additional homologs, variants and sequences are available to those of skill in the art using various databases including, for example, the National Center for Biotechnology Information (NCBI) access to which is available on the World-Wide-Web. Such homologs and variants can be identified by merely performing a BLAST search using a reference sequence from the present disclosure. For example, a BLAST search of ANME-1 mcrA gene (NCBI accession number CBH39484) using BLASTp algorithm yielded 9994 homologous or related protein sequences in about one minute performing the search, with identity ranging from 40% to 100%.

Culture conditions suitable for the growth and maintenance of a recombinant microorganism provided herein are known (see, e.g., "Culture of Animal Cells—A Manual of Basic Technique" by Freshney, Wiley-Liss, N.Y. (1994), Third Edition). The skilled artisan will recognize that such conditions can be modified to accommodate the requirements of each microorganism. Appropriate culture conditions useful in metabolizing methane and/or methanol comprise conditions of culture medium pH, ionic strength, nutritive content, temperature and other culture conditions that permit production of dissolved inorganic carbon by the host microorganism, i.e., by the $C_1$-metabolic action of the microorganism.

It is understood that a range of microorganisms can be modified to include a recombinant metabolic pathway or for the production of enzymes for use in a pathway suitable for the metabolizing methane and/or methanol. It is also understood that various microorganisms can act as "sources" for genetic material encoding target enzymes suitable for use in a recombinant microorganism provided herein.

The disclosure provides methods for the heterologous expression of one or more of the biosynthetic genes or polynucleotides involved in methane and/or methanol metabolism and recombinant DNA expression vectors useful in the method. Thus, included within the scope of the disclosure are recombinant expression vectors that include such nucleic acids.

Recombinant microorganisms provided herein can express a plurality of target enzymes involved in pathways for the production of dissolved inorganic carbon from a suitable carbon substrate such as, for example, methanol, methane, formaldehyde and the like. The carbon source can be metabolized to, for example, carbon dioxide. Sources of methanol, methane and formaldehyde are known. Of particular interest is methane gas, which occurs in nature and is a common by-product of waste degradation.

In another embodiment, a recombinant microorganism provided herein includes elevated expression of methyl-coenzyme M reductase (MCR) as compared to a parental microorganism. This expression may be combined with the expression or over-expression with other enzymes in the metabolic pathway for the production of carbon dioxide from methane. The methyl-coenzyme M reductase can be encoded by mcrA, mcrB, and mcrG genes, polynucleotides or homologs thereof. The mcrA, mcrB, and/or mcrG genes or polynucleotides can be derived from various microorganisms including methane-oxidizing archaea (ANME-1, 2 and 3).

In addition to the foregoing, the terms "methyl-coenzyme M reductase" or "MCR" refer to proteins that are capable of catalyzing the first step of the anaerobic oxidation of methane, and which share at least about 40%, 45%, 50%, 55%, 60%, 65%, 70%, 75%, 80%, 85%, 90%, 95%, 96%, 97%, 98%, 99% or greater sequence identity, or at least about 50%, 60%, 70%, 80%, 90%, 95%, 96%, 97%, 98%, 99% or greater sequence similarity, as calculated by NCBI BLAST, using default parameters, to one of the following sequences: ANME-1 MCR (Meyerdierks et al. 2010), mcrA: NCBI Accession Number CBH39484, mcrB: NCBI Accession Number CBH37405, mcrG: NCBI Accession Number CBH39483; ANME-1 MCR crystalized from Black Sea microbial mat (Shima et al. 2012), mcrA: PDB ID 3SQG Chain A, mcrB: PDB ID 3SQG Chain B, mcrG: PDB ID 3SQG Chain C; ANME-2a MCR (Wang et al. 2014), mcrA: IMG Gene ID 2566125579, mcrB: IMG Gene ID 2566125583, mcrG: IMG Gene ID 2566125580; Candidatus Methanoperedens *nitroreducens* MCR (Haroon et al. 2013), mcrA: NCBI Accession Number WP_048089615, mcrB: NCBI Accession Number WP_048089608, mcrG: NCBI Accession Number WP_048089613; Candidatus Bathyarchaeota archaeon BA1 MCR (Evans et al. 2015): mcrA, NCBI Accession Number KPV65186, mcrB: NCBI Accession Number KPV65184, mcrG: NCBI Accession Number KPV65185; Candidatus Bathyarchaeota archaeon BA2 (Evans et al. 2015), mcrA: NCBI Accession Number KPV61791, mcrB: NCBI Accession Number KPV61799, mcrG: NCBI Accession Number KPV61800.

Biological methane oxidation in the absence of oxygen is restricted to anaerobic methanotrophic archaea (ANME) that are phylogenetically related to methanogens. These organisms evolved to metabolize methane to $CO_2$ near thermodynamic equilibrium ($E^{o\prime}=-245$ mV for $CH_4/CO_2$) via the pathway of reverse methanogenesis or methane oxidation, which includes the chemically challenging step of methane activation without oxygen-derived radicals. Reported terminal electron acceptors for anaerobic oxidation of methane (AOM) include sulfate, nitrate, and metal oxides. Nitrate reduction coupled to methane oxidation is directly mediated by a freshwater archaeal methanotroph "Ca. Methanoperedens *nitroreducens*" ANME-2d; however, the electron transport mechanism coupling methane oxidation with other terminal electron acceptors (such as sulfate and metal oxides) is still debated.

Sulfate-coupled methane oxidation is the dominant mechanism for methane removal within marine sediments, preventing the release of teragrams per year of this greenhouse gas from the oceans:

$$CH_4+SO_4^{2-} = HCO_3^- + HS^- + H_2O (\Delta G^{o\prime}) = -17 \text{ kJ mol}^{-1}$$

Multiple methanotrophic archaeal lineages (ANME-1; ANME-2a,b,c; and ANME-3) form syntrophic consortia with sulfate-reducing bacteria (SRB) that drive AOM in areas of methane release at the seabed. The metabolism of AOM with sulfate appears to be partitioned between the two partners, requiring the exchange of electrons or intermediates. The mechanism underlying this syntrophic association has been studied using microcosm experiments [with AOM microorganisms exhibiting doubling times of 2 to 7 months], as well as through the application of stable isotope analyses, radiotracer rate measurements, metagenomics, metatranscriptomics, metaproteomics, and theoretical modeling.

Attempts to metabolically decouple the syntrophic association and identify the intermediate compound passaged between ANME archaea and their SRB partners have been unsuccessful when diffusive intermediates such as hydrogen, acetate, formate, and some redox active organic electron shuttles were used. Culture-independent evidence for direct interspecies electron transfer in sulfate-coupled AOM by members of the ANME and their SRB partners supports earlier genomic predictions of this process occurring in the methanotrophic ANME-1 and ANME-2.

Guided by the recent evidence of direct interspecies electron transfer from ANME-2 to SRB, it was determined whether artificial electron acceptors can substitute for the role of the SRB partner as a terminal oxidant or electron acceptor for AOM. Respiration of the artificial electron acceptor 9,10-anthraquinone-2,6-disulfonate (AQDS, $E^{o\prime}=-186$ mV) has been previously reported in methanogens. AQDS was tested as a sink for methane-derived electrons generated by the ANME archaea in incubations with deep-sea methane seep sediment. The stoichiometry of methane oxidation coupled to AQDS predicts the reduction of four equivalents of AQDS per methane:

$$CH_4+4AQDS+3H_2O \rightarrow HCO_3^- + H^+ + 4AQH_2DS$$
$$\Delta G^{o\prime}=-41 \text{ kJ mol}^{-1}$$

By using a combination of rate measurements and single-cell stable isotope probing, it has been shown herein that ANME in deep-sea sediments can be catabolically and anabolically decoupled from their syntrophic SRB partners using soluble artificial oxidants or electron acceptor. The ANME still sustain high rates of methane oxidation in the absence of sulfate as the terminal oxidant or electron acceptor, lending support to the hypothesis that interspecies extracellular electron transfer is the syntrophic mechanism for the anaerobic oxidation of methane.

It was hypothesized and demonstrated that redox active compounds that have the ability to accept single electrons could replace the role of the SRB partners during AOM. Several compounds were shown in the Examples section below, including AQDS isomers, humic acids, and iron(III) complexes, that could accept electrons from AOM and become reduced. The total number of electrons that the electron acceptor "Q" can take vary depending on the compound, and equations below show the stoichiometry that changes based on the molecule:

$$CH_4+8Fe(III)+3H_2O \rightarrow HCO_3^- + 9H^+ + 8Fe(II)$$

$$CH_4+4AQDS+3H_2O \rightarrow HCO_3^- + H^+ + 4AQH_2DS$$

$$CH_4+2 \text{ humic acid} + 3H_2O \rightarrow HCO_3^- + 9H^+ + 2 \text{ humic acid(reduced)}$$

The humic acid is commonly prepared by extraction from soils and/or commercially available, and contains of a mixture of redox active organic molecules of high molecular weight; a molecule that can accept 4 electrons total is shown above as an example.

Mechanistically, extracellular electron transfer from ANME-2 to single electron acceptors can account for the findings herein. Large, S-layer-associated multi-heme c-type cytochromes such as those in ANME-2a (IMG Gene ID 2566123487 and 2566125052), ANME-2b (NCBI Accession Number KR811028), ANME-2d or Methanoperedens *nitroreducens* (IMG Gene ID 2515322983, 2515320866) together with membrane and extracellular cytochrome b and/or c such as the one in ANME-2a (IMG Gene ID 2566125773 and 2566125774) could putatively conduct electrons derived from reverse methanogenesis or methane oxidation from the archaeal membrane to the outside of the cell, where they can be taken up by a suitable electron acceptor. A congruent path of extracellular electron transfer has been proposed for the bacterium *Geobacter sulfurreducens* when oxidizing acetate coupled to the reduction of AQDS or humic acids. The similar catabolic and anabolic activities observed within ANME-2 archaea, independent of whether the terminal electron acceptor is AQDS or sulfate, suggest that the biochemistry within these organisms may follow the same pathway under AQDS conditions as when syntrophically coupled to SRB. The data therefore also lend experimental evidence in support of the hypothesis of direct interspecies electron transfer as the syntrophic coupling mechanism between methane-oxidizing ANME-2 and SRB in the environment.

The apparent ability of ANME-2 to oxidize methane via the release of single electrons constitutes a versatile half-metabolism. This physiology suggests that methanotrophic ANME-2 archaea should also be able to respire solid electron acceptors directly via extracellular metal reduction, such as methane oxidation coupled to soluble iron(III) as shown in the Examples section below and insoluble iron(III) and manganese(IV) reduction. Evolutionarily, methane oxidation with metal oxides could have served as a transient life style for ANME before the establishment of a syntrophic association with SRB. According to this hypothesis, methanogenic archaea first evolved the capability to conserve energy as a methanotroph coupled with the respiration of solid metal oxides as electron acceptors. In a subsequent evolutionary step, SRB developed a symbiosis with ANME archaea, gaining a direct source of electrons for sulfate reduction and leading to the highly structured syntrophic consortia common today in seep environments. This physiology of using extracellular electron transfer to enable syntrophic interaction has the advantage that intermediates cannot be lost via diffusion and that electrical conductance is much faster than diffusive transfer of reducing equivalents. Further, this described metabolism may have industrial utility, providing a mechanism for the conversion of methane to $CO_2$ plus single electrons that can be catalyzed reversibly at low temperatures, with the potential to convert methane to electricity at high overall efficiencies.

Natural gas accounts for over 20% of the energy consumption worldwide. Its primary component, methane, is a renewable energy carrier, but it's conversion to electricity in fuel cells usually requires temperatures around 650° C. to cleave its inert C—H bonds. Efficient conversion of chemical energy to electricity must avoid such high-temperature processes. Biosystems containing the enzyme methyl-coenzyme M reductase (MCR) are an attractive alternative to convert methane at low temperatures reversibly to a methyl-group that can be used for downstream reactions.

In certain embodiments, the disclosure provides for a bioelectrochemical device that utilizes a bioreactor comprising a MCR-containing biosystem that is capable of converting methane from sources such as biomass or a fuel gas stream to electricity via an electron carrier "$QH_2$" as shown in the scheme presented as FIG. 13. In a particular embodiment, one or more steps presented in FIG. 13 proceed at ambient temperature so as to be energy efficient. Biomass fermentation and electricity generation from electron carriers have both received much attention in recent years for energy generation and storage purposes and now satisfy efficiency requirements. Yet, methane activation remains difficult to link these two processes. Recent results show that MCR-containing anaerobic methanotrophs can oxidize methane and generate soluble electron carriers. Anaerobic methanotrophs (ANME) are able to convert methane very efficiently to other forms of reducing equivalents via the enzyme methyl-coenzyme M reductase. In marine environments, those archaea perform methane oxidation anaerobically at 4° C. and transfer the electrons to bacteria that reduce sulfate to sulfide. The overall reaction of methane oxidation with sulfate yields≈−34 kJ mol$^{-1}$ under in situ conditions, which is substantially lower than aerobic methane oxidation that yields −810 kJ mol$^{-1}$. Recent physiological studies indicate that the methane-sulfate syntrophy is accomplished via "direct" electron transfer between the two partners. Hence, ANME catalyze the following reaction presented in the formula:

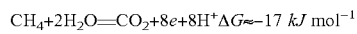

$CH_4 + 2H_2O = CO_2 + 8e + 8H^+ \Delta G \approx -17 \ kJ \ mol^{-1}$

This reaction can be used to generate a reduced artificial electron acceptor "$QH_2$" according to the following formula, at a metabolic rate comparable to the rate when coupled to sulfate:

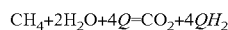

$CH_4 + 2H_2O + 4Q = CO_2 + 4QH_2$

The results of Eq. 4 have two important consequences: First, ANME can now be grown in pure cultures for genetics and functional studies. Second, it demonstrates that the metabolism of ANME can be used for the generation of artificial electron acceptors that permit energy-relevant applications. Therefore, the free energy for methane oxidation with oxygen ($\Delta G \approx -810 \ kJ \ mol^{-1}$) can be partitioned into a biochemical step for energy conversion followed by an electrochemical step to harvest the energy. An example is shown here with the artificial electron acceptor Q being 2,6-AQDS:

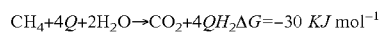

$CH_4 + 4Q + 2H_2O \rightarrow CO_2 + 4QH_2 \Delta G = -30 \ KJ \ mol^{-1}$

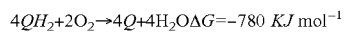

$4QH_2 + 2O_2 \rightarrow 4Q + 4H_2O \Delta G = -780 \ KJ \ mol^{-1}$

An example of a bioreactor with internal cycling of the artificial electron acceptor Q is shown in FIG. 14. In a certain embodiment, the bioreactors disclosed herein will utilize wild-type or engineered organisms for the efficient conversion of methane to reduced electron carriers. The advantages of such a system as well as with non-synthetic systems, include but are not limited to, increase in energy generation efficiency; scalable bioreactors that allow small-scale power capturing where gas turbines would be too big (biogas plants, replacement of gas flares, etc.); high dynamic range of power output that is ideal for the volatile methane source biogas; robust to impurities present in biogas such as $CO_2$ or volatile siloxanes; and electrons captured from methane can be used for alternative processes (e.g., $H_2$ production or chemical synthesis). Furthermore, as anaerobic methanotrophs are not available in pure culture and have doubling times of ca. 2-7 months under lab conditions, the disclosure further provides for modifying methanotrophs to increase the growth rate and/or increase the activity/expression of methyl-coenzyme M reductase, and/or amend the metabolism of a methanogen so as to increase metabolism of methane, and/or amend and engineer the metabolism of an aerobic methanotroph so as to perform anaerobic oxidation of methane as an alternative or additional metabolism to existing metabolisms in the host with higher metabolic rate. Standardly employed recombinant techniques can be used to achieve the foregoing, including the use of expression vectors, mutagenesis, etc.

Various aspects of the disclosure are generally directed to a bioelectrochemical device which comprises a fuel cell or other devices that use similar operating principles, for example, devices that are able to oxidize fuel to produce electrons. A fuel cell is a device that converts fuel to electrical energy without combustion of the fuel (although a fuel cell could be used in conjunction with a device deriving energy from combustion of the same fuel; most fuel cells do not). A typical fuel cell includes two electrodes, an anode and a cathode, an electrolyte in contact with both the anode and cathode, and an electrical circuit connecting the anode and the cathode from which power created by the fuel cell can be drawn. The anode and the cathode are typically contained within separate compartments, which may be separated by an interface or a barrier. In a particular embodiment, a fuel cell disclosed herein utilizes or is based upon an organic-inorganic aqueous flow battery described in Huskinson et al. (*Nature* 505:195-200 (2014)), which is incorporated in-full in this disclosure.

In one set of embodiments, the barrier may be formed from a metal, such as gold, palladium, or platinum, and in some cases, the barrier may be backed on one or both sides by an inert film, for instance, comprising a hydrophobic polymer such as polytetrafluoroethylene (Teflon), and/or the barrier may be composed of anion/cation/proton exchange membranes. Such a barrier may be used, in some cases, to allow the exchange of hydrogen gas and/or ions, but generally impede the exchange of other dissolved gases.

In some cases, the fuel cell may contain a plurality of anodes and/or cathodes, e.g., in the same or different compartments, which may be operated in series and/or in parallel.

In typical operation, an oxidant (e.g., oxygen, such as the oxygen found in the air, or bromine) is provided to a cathode of a fuel cell where it is reduced, e.g., to form water or hydrogen bromide, while a reduced electron acceptor ($QH_2$) in contact with the anode is oxidized, e.g., to produce an electron acceptor (Q). The electrons may be removed from the anode by a current collector, or other component of an electrical circuit, which results in an electrical current. The overall reaction may be energetically favorable, i.e., the reaction gives up energy in the form of electricity or power driving electrons from the anode, through electrical circuitry, to the cathode. This energy can be captured for essentially any purpose, e.g., for immediate use and/or for storage for later use.

The fuel cell may be fabricated from any suitable material. For example, in one set of embodiments, the fuel cell, or a portion thereof, such as an anode compartment, may be fabricated from non-conductive materials, for instance, from any polymer such as polyvinyl chloride, polyethylene, polypropylene, or polyethylene terephthalate. In another set of embodiments, the fuel cell (or portion thereof) may be formed from thermally insulating and/or non-conductive materials such as ceramics, glass, wood, and/or metals that may or may not be coated with thermal or electrical insulators, e.g. Teflon-coated aluminum, polymeric-coated steel, glass-lined stainless steel, etc. As discussed herein, in some embodiments of the disclosure, thermal insulators are useful for the management or retention of heat within the fuel cell, which may lead to higher power output.

In some aspects of the disclosure, the bioelectrochemical device of the disclosure comprises a fuel cell that is connected to bioreactor system comprising $C_1$ metabolizing microorganisms (e.g., ANMEs) that produce dissolved inorganic carbon from $CH_4$. In such a system, an electron acceptor/reduced electron acceptor can be cycled between the fuel cell and the bioreactor. Thus, the fuel cell uses the reduced electron acceptor produced from the bioreactor system to make electrical energy by oxidizing the reduced electron acceptor to an oxidized form, whereby the electron acceptor is then cycled back to the bioreactor to be reduced by the action of $C_1$ metabolizing microorganisms to form a reduced electron acceptor. In one set of embodiments, the fuel cell contains an anode and a cathode, each within different compartments. The cathode may be placed in a compartment with an abundance of oxygen (i.e. an aerobic environment), and/or in the presence of a soluble oxidant or electron acceptor such as nitrate, sulfate, iron oxide, manganese oxide, or other redox active compounds, while the anode may be placed in a second compartment having an environment that is deficient or devoid oxygen (i.e., an anaerobic environment), and/or other oxidants or electron acceptor including, but not limited to, soluble oxidants or electron acceptor such as nitrate, sulfate, iron oxide, manganese oxide, etc. In one embodiment, the anode contains a percentage of oxygen that is less than atmospheric oxygen, i.e., less than about 21% by total volume. Typically, the anode is fluidly in contact with a solution which comprises a reduced electron acceptor ($QH_2$). The source of methane that is converted to dissolved inorganic carbon by the microorganisms of the bioreactor can come from any number of sources, including from natural gas, syn gas, shale gas, town gas, etc. For example, the methane may be produced from materials such as chemical or industrial reactions, or biomass, i.e., matter derived from living biological organisms.

"Biomass," as used herein, may arise from plants or animals. For example, plants such as switchgrass, hemp, corn, poplar, willow, or sugarcane may be used as a fuel source to provide methane to the bioreactor disclosed herein via fermentative pathways utilizing methanogens. The entire plant, or a portion of a plant, may be used as the methane source, depending on the type of plant. As another example, biomass may be derived from animals, for instance, animal waste or animal feces, including human sewage (which may be used raw, or after some treatment). Still other non-limiting examples of biomass include food scraps, lawn and garden clippings, dog feces, bird feces, composted livestock waste, untreated poultry waste, etc. The biomass need not be precisely defined. In some cases, the biomass does not necessarily exclude fossil fuels such as oil, petroleum, coal, etc., which are not derived from recently living biological organisms, nor does it exclude refined or processed materials such as kerosene or gasoline.

FIG. 13 provides an exemplary flowchart of a process to convert methane to electricity using a bioreactor and fuel cell described herein.

FIG. 14 provides a schematic view of an exemplary bioelectrochemical device of the disclosure. Methane ($CH_4$) originating from methane source 5 is injected to inlet tube 25 to supply methane to the $C_1$-metabolizing microorganisms in bioreactor 10. Valve 20 is also provided to control the flow of methane into inlet tube 25.

In a particular embodiment, methane source 5 is a methane producing system from a fuel source such as biomass. Methane production is the consequence of a series of metabolic interactions among various groups of microorganisms. The first group of microorganisms secrete enzymes which hydrolyze polymeric materials found in biomass to monomers such as glucose and amino acids, which are subsequently converted to higher volatile fatty acids, $H_2$ and acetic acid. In the second stage, hydrogen-producing acetogenic bacteria convert the higher volatile fatty acids e.g., propionic and butyric acids, produced, to $H_2$, $CO_2$, and acetic acid. Finally, the third group, methanogenic archaea convert $H_2$, $CO_2$, and acetate, to $CH_4$ and $CO_2$. Methanogens are physiologically united as methane producers in anaerobic digestion. Although acetate and $H_2/CO_2$ are the main substrates available in the natural environment, formate, methanol, methylamines, and CO can also be converted to $CH_4$ by methanogenic archaea. In an alternate embodiment, methane source 5 is from a methane containing fuel gas stream, wherein the fuel gas stream may be enriched for methane by purifying the methane from other components of the fuel gas stream. Examples of a fuel gas stream include, but are not limited to, a natural gas stream, a shale gas stream, or a town gas stream. Inlet tube 25 can be comprised of any material. For example, inlet tube 25 can be comprised of metal, plastic or rubber. As the fluid running through inlet tube 25 is pressurized, inlet 25 should have a maximum burst pressure that exceeds, preferably greatly exceeds, the pressure being exerted by the fluid on the walls of inlet tube 25. While inlet tube 25 typically is an elongated cylindrical shape, it should be understood that inlet tube 25 can have any shape (e.g., square, hexagonal, triangular, etc.) as long as fluid can freely pass through the inside space of inlet tube 25. Valve 20 is provided to control the flow of methane into inlet tube 25. Typically, valve 20 is a check valve that only allows methane to flow through it. The body of valve 20 can be made of any material, but plastic or metal is preferred. Valve 20 can be any type of valve, including a ball valve, diaphragm valve, swing valve, tilting disc valve, stop-check valve, a lift valve, in-line valve, duckbill valve, etc. Moreover, although not depicted in FIG. 14, valve 20 can be a series of valves. For example, a double check valve is preferred.

For the exemplary bioelectrochemical device depicted in FIG. 14, it should be understood that an aqueous solvent is flowing through the various tubes, bioreactor, $CO_2$ separating device, and anode compartment of the fuel cell. Accordingly, methane injected into inlet tube 25 via methane source 5 mixes with the aqueous solvent present in inlet tube 25. The aqueous solvent comprises in addition to water any number of additional components, including buffers, salts, nutrients to support the growth of $C_1$-metabolizing microorganisms, etc. In particular, the aqueous solvent comprises an aqueous soluble electron acceptor. Any aqueous soluble electron acceptor can be used as long as the electron acceptor is a single-electron acceptor with a standard reduction potential more positive than ca. −240 mV. Specific examples of such electron acceptors include, but are not limited to, 2,6-AQDS (9,10-anthraquinone-2,6-disulfonate), 2,7-AQDS (9,10-anthraquinone-2,7-disulfonate), 1,5-AQDS (9,10-anthraquinone-1,5-disulfonate), Fe(III)-citrate, Fe(III)-EDTA, humic acids, and Melanin. In a particular embodiment, the aqueous solvent is substantially free or devoid of dissolved oxygen.

Turing to bioreactor 10 depicted in FIG. 14, bioreactor 10 comprises a housing and at least two ports an inlet port to receive the aqueous solvent from inlet tube 25, and an outlet port to pass the aqueous solvent from bioreactor 10 to outlet tube 30. It should be noted, that while solvent entering the bioreactor 10 is enriched with methane and an electron acceptor (Q), the solvent exiting the bioreactor 10 is enriched with $CO_2$ and other dissolved inorganic carbon (DIC) species and the reduced electron acceptor ($QH_2$), via the conversion of methane to the DIC species by the action of $C_1$-metabolizing microorganisms. Bioreactor 10 can comprise populations of one or more different types of $C_1$-metabolizing microorganisms. In a particular embodiment, bioreactor 10 comprises one or more species of methanotrophs. In a further embodiment, the population of one or more types of $C_1$-metabolizing microorganisms are grown or contained within a bed of media or solid support(s) in one or more compartments. The media and solid support should be made of a biologically inert material. Generally, the media and solid support comprises a high surface area so that $C_1$-metabolizing microrganisms can spread across the surface of the media or solid support. In a particular embodiment, the solid support is comprised of a porous or very porous material. Examples of porous materials, include but are not limited to, sponges, fibrous material, bio-balls, ceramic filters, and the like. In other embodiments, the $C_1$-metabolizing microorganisms can be grown on or contained within a media bed, wherein the solvent is forced through the media bed by pressure, or through the media bed by gravity, depending on the whether the inlet tube connects to the bioreactor at the bottom of bioreactor 10 as shown in FIG. 14, or at the top of bioreactor 10 (not shown). It should be noted in the latter case, the outlet tube 30 will be connected to the bottom of bioreactor 10. The media bed can be made from any particulate media including sand, gravel, or synthetic beads. Moreover, the media bed may comprise layers of media that are comprised of different materials, whereby the layers may or may not be physically in contact with each other (i.e., separated by an intervening layer that does not contain a media bed, such as a membrane). In further embodiments, the housing of bioreactor 10 comprises two surfaces, and inner surface that comes into contact with the aqueous solvent and an outer surface that does not come into contact with the aqueous solvent. Moreover, in certain embodiments, the outer and inner surface may comprise different materials. Typically, the bioreactor vessel is made of stainless steel or high grade plastic. In a further embodiment, the inner surface of the bioreactor vessel may comprise borosilicate glass. Bioreactor 10 may further comprise any number of other components including agitators, baffles and a jacket. Agitators are used for the mixing of the contents of the reactor which keeps the $C_1$-metabolizing microorganisms in the perfect homogenous condition for better transport of nutrients and methane to the microorganisms. The agitator can be magnetically or mechanically driven. Baffles can be used to break the vortex formation in the vessel. A jacket can be used to maintain the temperature of the bioreactor at a constant value. Bioreactor 10 may further comprise one or more filters or membranes to prevent the passage of solid material (e.g., microorganisms, cellular debris, etc.) into and/or out of bioreactor 10.

Turing to outlet tube 30 and $CO_2$ separator 35 depicted in FIG. 14. The aqueous solvent exiting bioreactor 10 is enriched with DIC, such as $CO_2$, and the reduced electron acceptor. The solvent is passed into outlet tube 30 from bioreactor 10 and then passed into $CO_2$ separator 35. Outlet tube 30 can be comprised of any material. For example, inlet tube 30 can be comprised of metal, plastic or rubber. As the fluid running through outlet tube 30 is pressurized, outlet tube 30 should have a maximum burst pressure that exceeds, preferably greatly exceeds, the pressure being exerted by the fluid on the walls of outlet tube 30. While outlet tube 30 typically is an elongated cylindrical shape, it should be understood that outlet tube 30 can have any shape (e.g., square, hexagonal, triangular, etc.) as long as fluid can freely pass through the inside space of outlet tube 30. $CO_2$ separator 35 is provided as a means to remove $CO_2$ and possibly other DICs from the aqueous solvent, thereby providing an impetus under Le Chatelier's principle to drive methane conversion by the $C_1$-metabolizing microorganisms and to eliminate pressure and pH effects resulting from $CO_2$ buildup in the aqueous solvent. Separator 35 may be placed before (as in FIG. 14) or after the fuel cell. Examples of devices that can be used for $CO_2$ separator 35 include membrane degasifiers, vacuum degasifiers and $CO_2$-precipitating chemical reactors. Vacuum degasifiers use reduced pressure to extract $CO_2$ from the aqueous solvent. While membrane degasifiers also use a vacuum to remove $CO_2$, but employ hollow fibers that have pores that allow the passage of gases like $CO_2$, but not the aqueous solvent, so that dissolved $CO_2$ in the aqueous solvent is forced through the hollow fiber pores and is carried away by a vacuum pump (see FIG. 15). Both membrane degasifiers and vacuum degasifiers are available commercially by any number of vendors, and are available in compact or very large industrial sizes (e.g., Liqui-Cel® Membrane Contractors). In a particular embodiment, $CO_2$ separator 35 is a membrane degasifier. In another embodiment, the $CO_2$ separator 35 is a $CO_2$-precipitating chemical reactor can be used employing precipitating chemical reactions to lower dissolved $CO_2$ in the aqueous solvent, by changing pH, alkalinity, temperature, pressure, agitation, dissolved ion or seed crystal concentration etc. Example anions that form precipitant with carbonate in a chemical reaction include but not limited to calcium, magnesium, iron, zinc, barium, strontium, cadmium, manganese, cobalt, and mixtures of two or more of these anions.

Turing to fuel cell 40 depicted in FIG. 14. After $CO_2$ and other DIC species are removed from the aqueous solvent, the degassed aqueous solvent comprising reduced electron acceptor ($QH_2$) is then passed into anode compartment 45 of fuel cell 40. Fuel cell 40 comprises anode 50, anode compartment 45 cathode 60, cathode chamber 62 and ion conductor 55. Fuel cell 40 allows positively charged hydrogen ions (e.g., protons) to move between the two sides of the fuel cell using commercially available proton exchange membrane, and/or other positively or negatively charged ions using commercially available anion or cation exchange membranes. Anode 50 contains catalysts that cause the reduced electron acceptor ($QH_2$) to undergo an oxidation reaction by coming into contact with anode 50. Therefore, $QH_2$ is oxidized to an electron acceptor (Q) in the process, as well as generating hydrogen ions and electrons. The hydrogen ions are drawn through or balanced by a transfer of other positively or negatively charged ions from anode chamber 45 to cathode chamber 62 via conductor 55 after the reaction. At the same time, electrons are drawn from anode 50 to cathode 60 through an external circuit, producing direct current electricity which may be stored or used accordingly. In the cathode compartment 62, hydrogen ions, electrons, and oxygen react at the cathode 60 to form water in the case of using oxygen as oxidant, or bromine ($Br_2$) react at the cathode 62 to form hydrogen bromide (HBr) in the case of using Br2 as oxidant for example. Cathode compartment 62 can be filled with a fluid or a mixture of fluids, wherein the fluid(s) comprise one of more oxidants (e.g., pure oxygen and oxygen-containing gases, like air; halogens e.g. bromine, chlorine; and/or other compounds, like $H_2O_2$, $MNO_4^-$, $VO_2$, $ClO^-$, and cerium ammonium nitrate). Examples of catalysts that can be used for anode 50 and cathode 60, include platinum or platinum ruthenium alloys dispersed in carbon powder. Examples of proton conductor 55 include proton-conductive polymer films as well as anion/cation exchange membranes like Nafion® and Fumapem® polymer films. Proton conductor 55 performs both as a separator and as a solid electrolyte in fuel cell 40 by selectively transporting hydrogen ions or other charged ions across the cell junction.

The aqueous solvent that exits anode compartment 45 of fuel cell 40 into fuel cell outlet tube 65 is enriched with an electron acceptor (Q), i.e., a product of the oxidation reaction at anode 50. The solvent in fuel cell outlet tube 65 can then be analyzed and supplemented/adjusted via the medium inlet and outlet valve 67. Typically, medium inlet and outlet valve 67 is a check valve that allows fluid (liquid or gas) to flow through it in only one direction. The medium inlet and outlet valve 67 can be made of any material, but plastic or metal is preferred. Medium inlet and outlet valve 67 can be any type of valve, including a ball valve, diaphragm valve, swing valve, tilting disc valve, stop-check valve, a lift valve, in-line valve, duckbill valve, etc. The aqueous solvent in fuel cell outlet tube 65 is then pumped into inlet tube 25 via pump 70. Fuel cell outlet tube 65 can be comprised of any material. For example, fuel cell outlet tube 65 can be comprised of metal, plastic or rubber. As the fluid running through fuel cell outlet tube 65 is pressurized, fuel cell outlet tube 65 should have a maximum burst pressure that exceeds, preferably greatly exceeds, the pressure being exerted by the fluid on the walls of fuel cell outlet tube 65. While fuel cell outlet tube 65 typically is an elongated cylindrical shape, it should be understood that fuel cell outlet tube 65 can have any shape (e.g., square, hexagonal, triangular, etc.) as long as fluid can freely pass through the inside space of fuel cell outlet tube 65. Pump 70 is used to drive the re-circulation of the aqueous solvent through the bioelectrochemical device. Pump 70 can be any type of standard pump, including, but not limited to, centrifugal pumps, ANSI process pumps, API process pumps, axial flow pumps, booster pumps, circulator pumps, magnetic drive pumps, diaphragm pumps, peristaltic pumps, piston pumps, plunger pumps, and screw pumps.

It should be noted that one or more of the components of a bioelectrochemical device disclosed herein may be manually and/or electronically controlled. Thus, the opening of values, operation of pumps, etc. may be controlled directly and/or remotely across a network or by wireless communication (e.g., bluetooth) via a computer, cell phone, tablet, terminal, and the like.

The invention is illustrated in the following examples, which are provided by way of illustration and are not intended to be limiting.

EXAMPLES

Sediment collection and processing. Santa Monica basin seep sediments overlain by a white mat were collected from the Santa Monica Mounds site in a push core (PC 61) deployed by the ROV Doc Ricketts. Samples were collected in May 2013 during a research cruise organized by the Monterey Bay Aquarium Research Institute (MBARI) using the R/V Western Flyer. PC61 was collected during dive 463 at 860 m depth with an in situ temperature of 4° C. (lat. 33.78905, long. −118.66833). The intact sediment core was extruded shipboard and then heat-sealed in a large mylar bag flushed for 5 minutes with argon. Sediments were stored at 4° C. until processed in the lab (40 days after collection). The whole push core (ca. 12 cm, yielding 800 mL wet sediment) was suspended in 1600 mL filter sterilized $N_2$ sparged bottom seawater from the site (1 in 3 ratio) in an anaerobic chamber (3% $H_2$ in $N_2$). The anaerobic sediment slurry was then distributed into three 1 L pyrex bottles, sealed with a large butyl rubber stopper, and pressurized with methane (0.25 MPa). Aggregate counts at the start of the experiment were determined by DAPI staining and epifluorescence microscopy, yielding approximately 9.7× $10^5$ aggregates per mL wet weight sediment. The initial sulfate-coupled AOM activity of the sediment was assessed via sulfide production measurements, showing the generation of 2.8 mM sulfide within the first 15 days.

All manipulations of the sediment incubations were done anaerobically at 4° C. or on ice. Prior to establishment of the microcosm experiments, the seep sediment was maintained for 12 months at 4° C. under methane (0.25 MPa) in anoxic bottom seawater that was exchanged every 3 months. For all reported experiments in this study, the seawater above the sediment was exchanged with a modified artificial seawater (see below) that contained 10× less $Ca^{2+}$, no sulfate, no sulfide, and 25 mM HEPES buffer at pH 7.5. The low $Ca^{2+}$ concentration and lower pH prevent carbonate precipitation, which allows quantitative analysis of the $^{13}$C-bicarbonate formed in solution during $^{13}$C-methane oxidation. Methane was added (0.30 MPa), shaken and the sediment allowed to settle for 48 hours (sediment/total volume=1:3). The supernatant was exchanged 3 times with the described medium following the same procedure in order to obtain sulfate and sulfide-free sediment.

Medium Composition. The final composition in the medium was: NaCl 457 mM, $MgCl_2$ 47 mM, $Na^+$-HEPES (pH=7.5) 25 mM, KCl 7.0 mM, $NaHCO_3$ 5.0 mM, $CaCl_2$ 1.0 mM, $K_2HPO_4$ 1.0 mM, $NH_4Cl$ 1.0 mM, $SeO_3^{2-}$ 0.01 µM, $WO_4^{2-}$ 0.007 µM, 0.1% trace element solution, containing per liter: nitrilotriacetic acid 150 mg, $MnCl_2 \times 4$ $H_2O$ 610 mg, $CoCl_2 \times 6\ H_2O$ 420 mg, $ZnCl_2$ 90 mg, $CuCl_2 \times 2\ H_2O$ 7 mg, $AlCl_3$ 6 mg, $H_3BO_3$ 10 mg, $Na_2MoO_4 \times 2\ H_2O$ 20 mg, $SrCl_2 \times 6\ H_2O$ 10 mg, NaBr 10 mg, KI 70 mg, $FeCl_3 \times 6\ H_2O$ 500 mg, $NiCl_2 \times 6\ H_2O$ 25 mg. No vitamins, indicators, reducing agents, or other substances were added.

The sulfate concentration of the final sediment slurry was below detection limit (<10 μM). Before the start of the microcosm experiments, the sediment slurry was flushed with methane (ca. 20 min) to remove traces of sulfide. The presence of sulfide can chemically reduce AQDS, preventing methane oxidation with AQDS. It is possible that under these conditions, AOM is inhibited by the polysulfides formed from sulfide+AQDS rather than directly by reduced AQDS, as reduced AQDS was observed to accumulate in the experiments with no apparent inhibition of AOM (see TABLE 2A). For Table 2, the concentrations measured after a 21-day incubation (experiments in FIG. 1A) and calculated stoichiometry per DIC formed from methane.

TABLE 2

Final concentration of reduced electron acceptors $AQH_2DS$ and sulfide.

A) Final concentrations of reduced AQDS ($AQH_2DS$): DIC formed

| Experiment | [mM] | $AQH_2DS$ [mM] | Stoichiometry* |
|---|---|---|---|
| AQDS 10 mM | 2.39 | 8.6 | 3.60 |
| AQDS 10 mM | 2.64 | 9.6 | 3.62 |
| AQDS 10 mM + $MoO_4^{2-}$ 25 mM | 2.82 | 9.8 | 3.45 |
| AQDS 10 mM + $MoO_4^{2-}$ 25 mM | 2.59 | 9.2 | 3.55 |

B) Final concentrations of sulfide: DIC formed

| Experiment | [mM] | sulfide [mM]* | Stoichiometry† |
|---|---|---|---|
| Sulfate 28 mM (A) | 6.44 | 5.9 | 0.92 |
| Sulfate 28 mM (B) | 7.77 | 6.5 | 0.84 |
| Sulfate 28 mM (C) | 7.51 | 7.0 | 0.93 |
| Sulfate 28 mM (D) | 7.29 | 6.1 | 0.84 |

*The lower amount of $AQH_2DS$ found than expected (4:1 stoichiometry) may be attributed to partial oxidation during the process of sampling and titration.
*sulfide [mM] = sum of $HS^-$ and $H_2S$.
†The lower amount of aqueous sulfide measured relative to the expected 1:1 stoichiometry may be attributed to a combination of factors resulting in a loss of sulfide. These include some sulfide partitioning into the headspace as gaseous $H_2S$ and possibly escaping as gaseous $H_2S$ during sampling, partial sulfide oxidization during the sampling and centrifugation on the benchtop, or possibly precipitation with divalent cations during the incubation.

Figure 5:
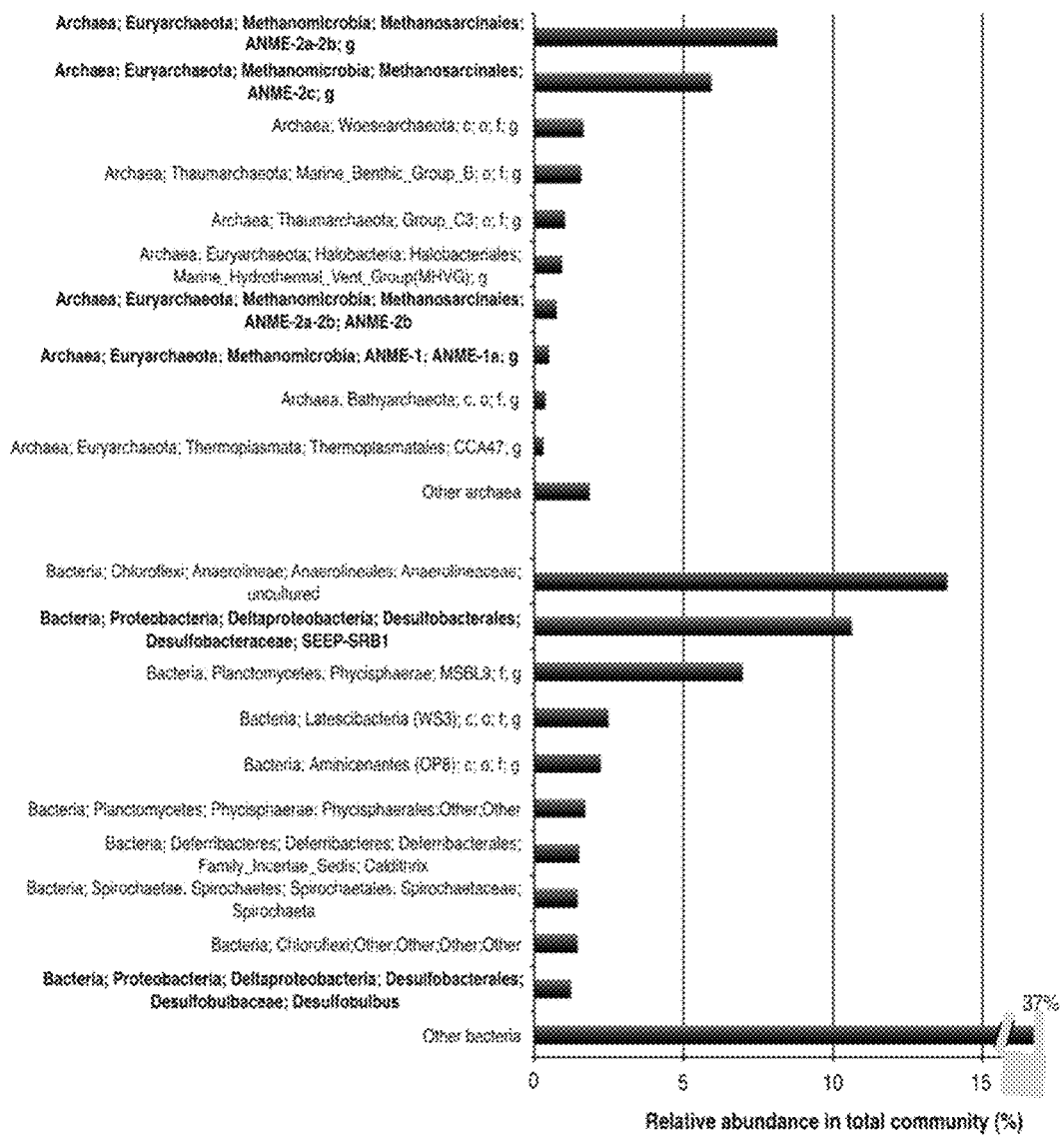
FIG. 5 presents the top 10 most abundant archaeal and bacterial genera in PC61. 16S rRNA gene Illumina TAG sequencing of the microbial assemblage in the initial PC61 sediment used for the microcosm experiments. Sequences were classified using the SILVA database release 119.

Sediment Characterization. AOM rates with sulfate (1.5 μmol methane (cm$^3$ wet sediment)$^{-1}$ d$^{-1}$) were comparable to active methane-seep sediments described previously. The dominant groups of archaea included ANME-2a and ANME-2c based on Illumina Tag sequencing using the Earth Microbiome primer set (FIG. 5). FISH hybridization and aggregate counts based on DAPI staining yielded 47% (69 of 146 aggregates) ANME-2a affiliated consortia and 43% ANME-2c (47 of 109 DAPI stained aggregates). The remaining 10% of aggregates likely represented other ANME not targeted by the specific FISH probes or possibly weakly hybridized ANME-2a or 2c aggregates that were below detection by FISH.

Chemicals and reagents. AQDS (=2,6-AQDS, >98% purity) and Fe(III)-EDTA was purchased from Sigma. Humic acids (sodium salt, tech. batch no. 10121HA) were obtained from Aldrich. 2,7-AQDS and 1,5-AQDS (>98% purity) were purchased from TCI chemicals. The different AQDS isomers were found to contain variable amounts of residual sulfate as determined by Ion Chromatography: 11 μM sulfate per 10 mM AQDS; 176 μM sulfate per 10 mM 2,7-AQDS; 344 μM sulfate per 10 mM 1,5-AQDS. 1,5-AQDS was re-crystallized from boiling water to remove traces of sulfate present in the purchased product. Residual sulfate in the re-crystallized 1,5-AQDS: 13 μM per 10 mM 1,5-AQDS. 2,7-AQDS, AQDS and all other chemicals were used as received. 50 mM Fe(III)-citrate stock solution was prepared by dissolving 2.0 mmol citric acid in a small amount of DI water, followed by the addition of 1.0 mmol $FeCl_3 \times 6\ H_2O$ and pH adjustment to pH=7.5 with NaOH. The solution was then diluted to 50 mM ferric ions (20 mL final volume).

General description of methane oxidation measurements via $^{13}C$-methane. Methane oxidation was quantified by determining the production of inorganic carbon ("$CO_2$"). Accurate quantification of the concentration of inorganic carbon formed from methane oxidation is challenging due to 4 main reasons:
(1) Inorganic carbon is present as a mixture of $CO_2$ (g) in the headspace, and $CO_2$ (aq.), $H_2CO_3$, $HCO_3^-$ or $CO_3^{2-}$ in solution (dissolved inorganic carbon, DIC); (2) Inorganic carbon may also be produced from respiration of organic carbon sources other than methane (3) Inorganic carbon can also be slowly produced via dissolution of carbonates (a major component of seep sediments); and (4) Inorganic carbon may also precipitate with divalent cations as insoluble carbonates.

It was found in the experiments, that quantifying methane oxidation using the stable isotope tracer $^{13}CH_4$ in incubations with a known amount of unlabelled (dissolved inorganic carbon, DIC) was the most accurate in analyzing the $^{13}C$ enrichment in DIC (see FIG. 3A). A defined amount of added DIC in artificial, buffered seawater was used with a low calcium concentration to prevent carbonate precipitation (see medium composition). As $^{13}CH_4$ was the only $^{13}C$-enriched carbon source added, the newly formed $^{13}C$-DIC must be derived from methane. For low methane oxidation rates (less than ca. 5% relative to sulfate as the oxidant or electron acceptor), however, enzyme-catalyzed isotope exchange between methane and DIC, needs to be taken into account, because it contributes to $^{13}C$ enrichment of the DIC without net methane oxidation, resulting in an overestimation of net methane oxidation. To illustrate the utility of this approach for quantifying rates of AOM, 2 AOM incubations were amended with $^{13}C$-methane and sulfate and compared with the calculation of newly formed DIC based on $^{13}CH_4$ (see FIG. 3B, red) with an independent method used in analytical chemistry based on standard addition that yields the absolute amounts of DIC formed during the incubations more directly (see FIG. 3B, black). Details of both methods, the $^{13}CH_4$ experiments and the standard addition are described herein. The method via standard addition provides evidence for net DIC increase during incubations, and is consistent with the progressive enrichment of $^{13}C$-DIC observed from $^{13}CH_4$. In this comparative analysis, however, it was observed an initial decrease in the absolute concentration of DIC within the first 2 days for the standard addition method, which are mainly attributed to diffusion of $CO_2$ into the headspace of the vial (see FIG. 3B, black).

Incubation conditions for AOM rate measurement. Each incubation vial was set up with 1.0 cm$^3$ wet sediment (wet sediment=volume of sediment after allowing the sediment slurry settle for 48 h) in total slurry volume of 5 mL as follows: Sterile serum vials were closed with butyl rubber stoppers (volume=12.9 ml after closing) and flushed with methane. 1.0 mL $^{13}CH_4$ (99% $^{13}C$, Cambridge Isotope Laboratories, containing 0.05 vol % $^{13}CO_2$ as an impurity) was introduced anaerobically. 2.0 mL of artificial, anaerobic seawater containing 2.5× the target concentration of the corresponding electron acceptor was injected into the serum vial cooled on ice. For AQDS and 1,5-AQDS, this was a suspension corresponding to 25 mM (see TABLE 3).

TABLE 3

Solubility of different AQDS regioisomers in the incubation medium.

| Compound | 4° C. | 22.5° C. |
|---|---|---|
| 2,6-AQDS (AQDS) | 0.9 mM | 1.9 mM |
| 2,7-AQDS | >25 mM | >25 mM |
| 1,5-AQDS | 2.5 mM | not determined |

The 1 L pyrex bottle with the sediment in the sulfate-free medium (1 part wet sediment in 3 parts of slurry volume) was vigorously shaken each time and 3.0 mL of slurry immediately removed and injected into the individual serum bottles. Each stoppered serum vial was supplemented with unlabeled methane (0.250 MPa overpressure: pressure gauge SSI Technologies, Inc., Media Gauge™) shaken and stored inverted at 4° C. (final headspace: 0.35 MPa methane, with ca. 4% $^{13}CH_4$). The exact fractional abundance of $^{13}C$ in the methane was quantified via $^1$H-NMR spectroscopy for individual incubations.

Figure 6:
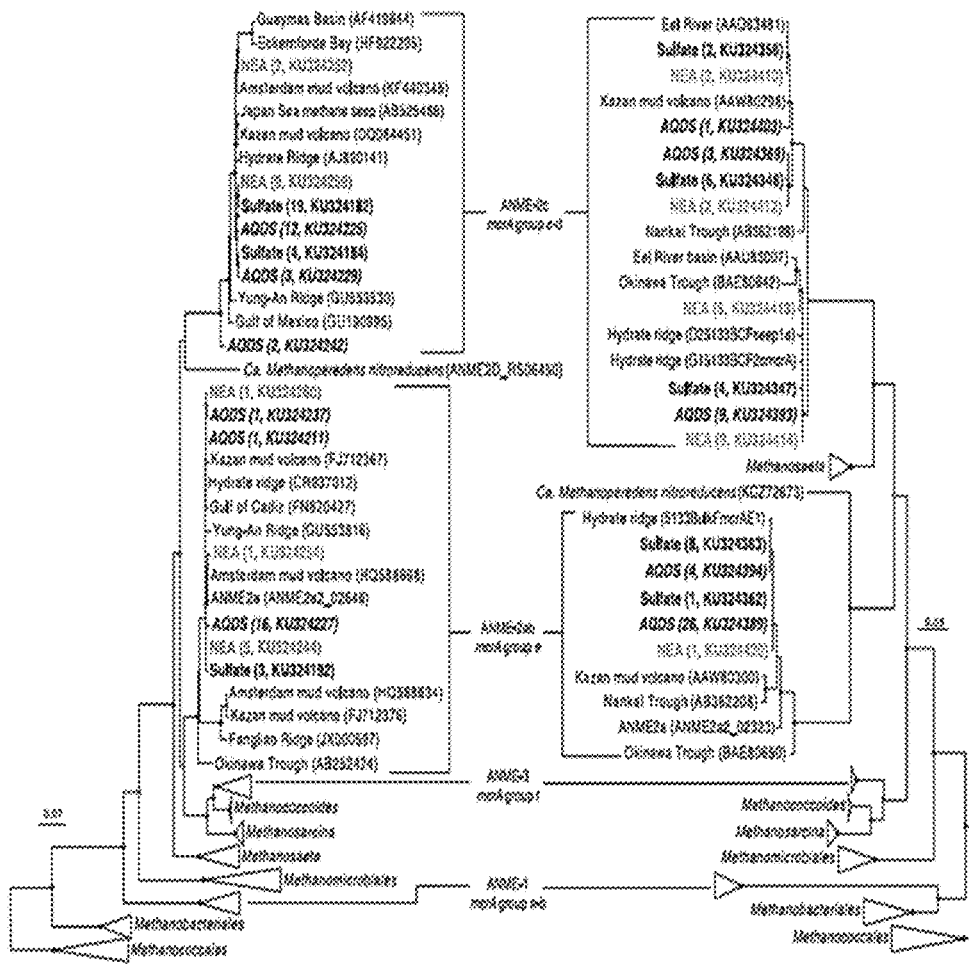
FIG. 6 presents the Bayesian phylogeny of expressed archaeal RNA recovered from different AOM microcosms. 16S rRNA (left) and mcrA (right) transcripts obtained from AOM incubations with either sulfate or AQDS as the primary oxidant or electron acceptor (bold text) or no electron acceptor added (NEA, gray text). Numbers in parentheses represent numbers of sequences recovered for each taxa. Bayesian likelihood values >75 and >90% are indicated by open and solid circles, respectively. Scale bars represent estimated sequence divergence or amino acid changes.

AOM rate measurements (quantification of newly formed DIC based on $^{13}CH_4$). For $^{13}C$-DIC analysis, 0.25 mL of the medium above the settled sediment in the microcosm was sampled with a disposable needle and syringe at each time point (same intervals for all experiments) and centrifuged (16000 rcf, 5 min). The supernatant was transferred into 0.6 mL eppendorf tubes, flash frozen in $N_2$ (l), and stored at −20° C. until measurement. 150 µL of the thawed supernatant was then added to He-flushed vials containing 100 µL $H_3PO_4$ (85%). The resulting $CO_2$ was analyzed for the isotopic enrichment ($^{13}F(t_n)$) on a GC-IR-MS GasBench II (Thermo Scientific). The amount of DIC newly formed ($\Delta[DIC](t_n)$, see FIG. 6B) was calculated from the measured $^{13}F$ (fractional abundance of $^{13}C$), neglecting isotope effects on AOM according to Equation (1):

$$\Delta[DIC](t_n)=[DIC](t_0)*(^{13}F(t_n)-^{13}F(t_0))/(^{13}F(CH_4)-^{13}F(t_n)) \quad (EQ. 1)$$

[DIC]=sum of carbonate, bicarbonate and $CO_2$, [DIC]$(t_0)$=5.0 mM $^{13}F(t_0)$=0.01153 (higher than medium due to $^{13}CO_2$-impurity in the $^{13}CH_4$ used)

Figure 2A:
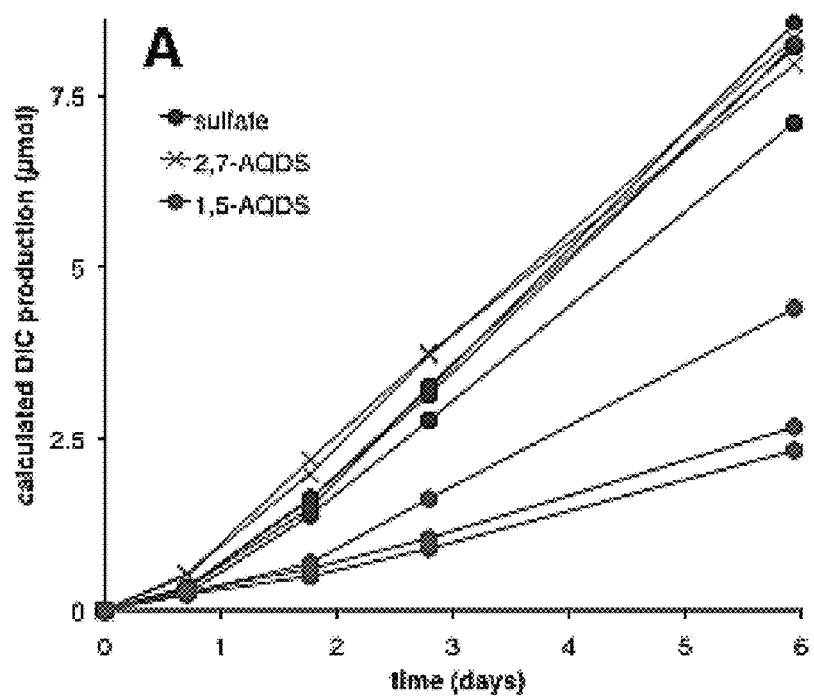
FIG. 2A-C shows the anaerobic oxidation of methane (AOM) with different oxidants or electron acceptors. (A) 2,7-AQDS and 1,5-AQDS; (B) Fe-citrate, various concentrations, and Fe-EDTA; and (C) humic acids, various concentrations. Time courses for rates described in FIG. 1B (lighter gray curves); AOM rates with sulfate are included as a reference (darker gray curves, representing identical data as shown in FIG. 1A).
Figure 2B:
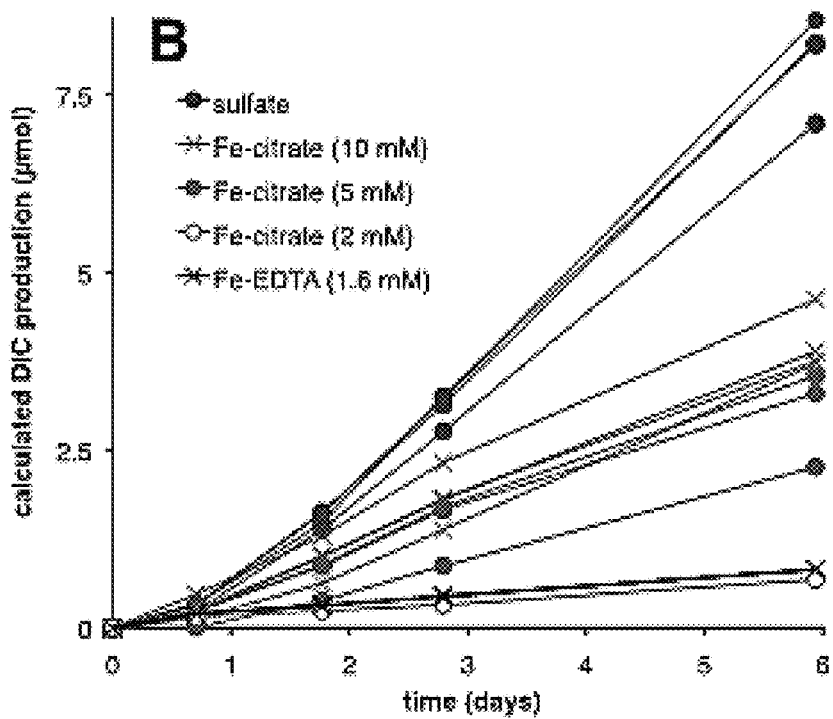
Figure 2C:
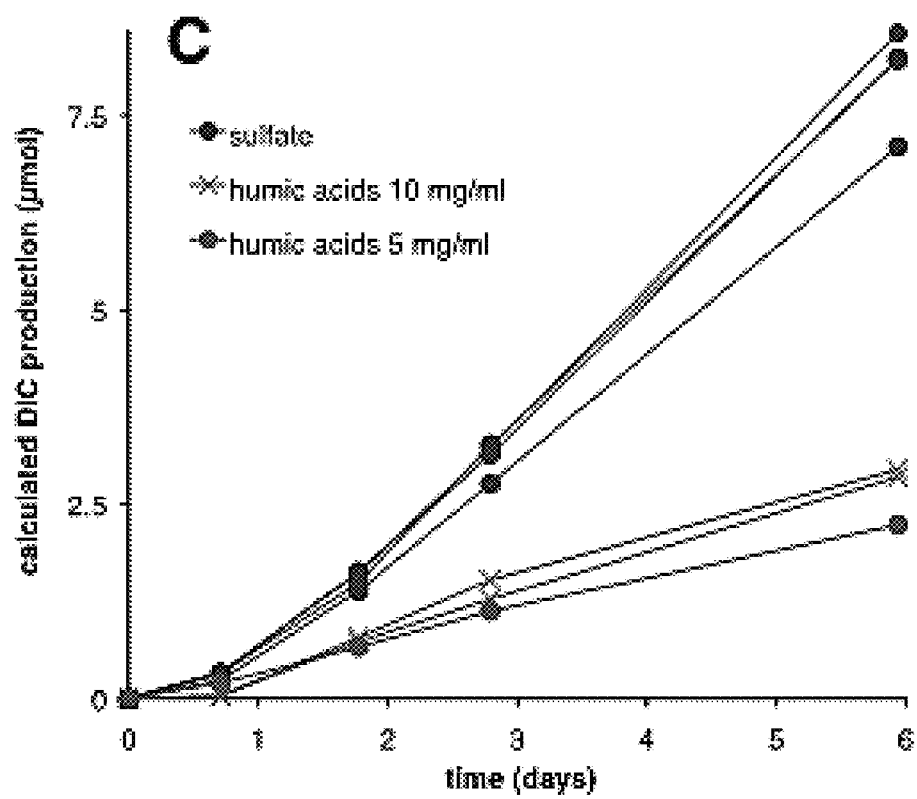
Figure 4:
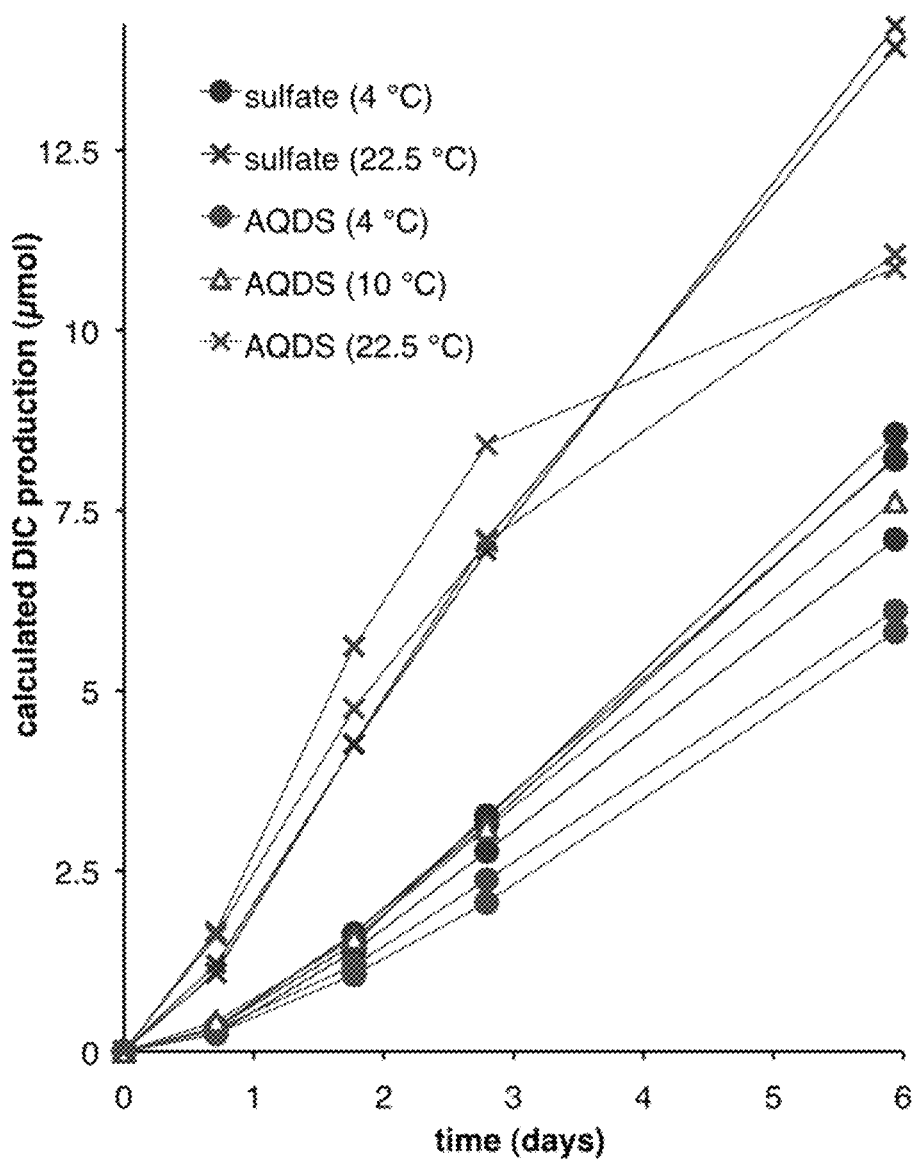
FIG. 4 provides a time course of AOM with sulfate and AQDS at 22.5° C. Data from experiments at 4° C. included as a reference (•symbol, identical data as in FIG. 1A).

$^{13}F(CH_4)=^{13}C$ in the methane used (measured via $^1$H-NMR spectroscopy). The amount of DIC formed per vial (See FIGS. 1A, 2, and 4) was calculated according to Equation (2):

$$DIC_{total}=5\ mL * \Delta[DIC](t_n) \quad (EQ. 2)$$

Figure 1B:
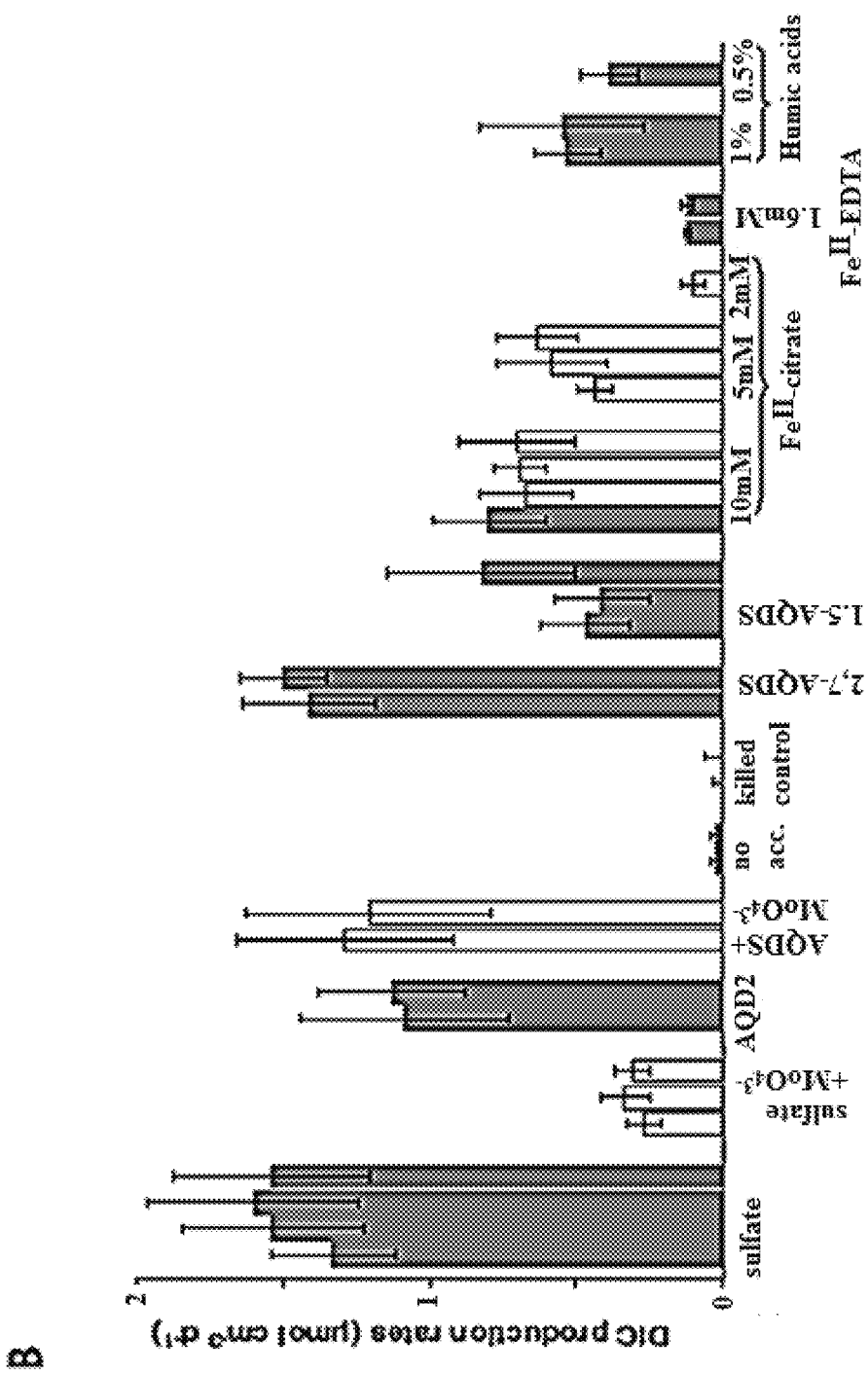

Calculation of specific AOM rates per volume sediment. For each incubation, the methane oxidation rate per volume sediment slurry was determined via linear regression of the time points 1, 2, 3 and 4 (17 h, 42.5 h, 67 h and 142.5 h). The 95% confidence intervals were calculated. Rates per cm$^3$ wet sediment are 5× higher than for the sediment slurry (sediment+modified HEPES-buffered seawater), as displayed in FIG. 1B (wet sediment=20% of total slurry volume).

Quantification of absolute DIC concentrations via standard addition. For two incubations with sulfate, quantified the absolute concentrations of DIC were quantified for the full time course of the incubations (see FIG. 3B) using the standard addition method. 75 µL of each sample was mixed with 75 µL of a DIC standard (10.0 mM NaHCO$_3$) and analyzed for its isotopic enrichment ($^{13}F_{mix}(t_n)$). The absolute DIC-concentration of the sample ([DIC]$(t_n)$), see FIG. 3B) was calculated according to Equation (3):

$$[DIC](t_n)=10\ mM*(^{13}F_{mix}(t_n)-^{13}F_{std})/(^{13}F(t_n)-^{13}F_{mix}(t_n)) \quad (EQ. 3)$$

Quantification of fractional abundance of $^{13}CH_4$ in the headspace used. The exact fraction of $^{13}CH_4$ (ca. 4.0%) was quantified for individual incubations at the end of the 21-day incubation period via $^1$H-NMR spectroscopy (Varian 400 MHz Spectrometer with broadband auto-tune OneProbe). Methane in the headspace was passed through deuterated chloroform (99.8% D, Cambridge Isotope laboratories) via a long 23 G needle and acquired at 400 MHz with a repetition time of 10 s. Fractional abundances of $^{13}C$ in the methane were obtained via integration of the $^{12}CH_4$ signal and of the $^{13}CH_4$-satellites (iNMR version 4.3.0).

Quantification of residual sulfate. Residual sulfate was quantified via Ion chromatography on a DX-500 or DX-2000 instrument (Dionex, Sunnyvale, Calif., USA) housed at the Caltech Environmental Analysis Center following the protocol outlined in Green-Saxena et al. (*Isme J.* 8:150 (2014)). The DI water used throughout this study contained <10 µM residual sulfate. Incubations with 2,7-AQDS contained a maximum of 200 µM residual sulfate, from traces of sulfate present in the purchased material (176 µM per 10 mM 2,7-AQDS), which could not be removed via re-crystallization due to the high solubility of 2,7-AQDS (described in the chemicals and reagents section above). For all other incubations, the sulfate concentration remained below 50 µM throughout the incubation period.

Quantification of sulfide. Supernatant was removed via syringe and centrifuged in 0.6 mL Eppendorf tubes (16000 rcf, 30 s). 20 µL of the clear supernatant was removed and added to 400 µL Zn(OAc)$_2$ (500 mM) to preserve the sulfide. Analysis was carried out in triplicate via the methylene blue method described in J. D. Clin (Waters. *Limnol. Oceanogr.* 14:454 (1969)), using standards of 0.1, 0.25, 0.5, 1, 2, 5, 10 and 25 mM sulfide added to Zn(OAc)$_2$ (500 mM) in the same ratios as for the samples. Quantification was carried out in a plate reader (TECAN Sunrise™) by monitoring the absorbance at 670 nm.

Quantification of AQDS solubility in the incubation medium. Different regioisomers of AQDS (1,5-AQDS, 2,6-AQDS and 2,7-AQDS) were separately added to the modified artificial seawater described above, to a targeted final concentration of 25 mM. The suspensions were ultra-sonicated at room temperature to dissolve as much of the AQDS as possible. The tubes were kept at 4° C. or at 22.5° C. overnight. The tubes were centrifuged at 4° C. or 22.5° C. (16000 rcf, 30 min). The supernatant (300 µL) was mixed with 300 µL acetate (10.0 mM) as the internal standard and 100 µL deuterated water (99.9% D, Cambridge Isotope Laboratories) was added. The concentration of AQDS was obtained from integration of the $^1$H-NMR spectra by comparison relative to the acetate standard.

Identity of reduced AQDS by UV-Vis and NMR. Reduced AQDS was identified photospectrometrically matching the spectra reported previously by Gamage et. al. (*J. Chem. Soc.-Faraday Trans.* 87:3653 (1991)). Solutions containing reduced AQDS were paramagnetic (ca. 1000 Hz line width, $^1$H-NMR spectroscopy), putatively due to the presence of the semiquinone-radical. Supernatant from an incubation that contained ca. 10 mM reduced AQDS was sparged with air for 30 min in order to re-oxidize AQH$_2$DS back to AQDS. $^1$H-NMR spectroscopy shows full conversion to AQDS, undistinguishable from the AQDS used initially. No signals other than AQDS or HEPES buffer were visible in the spectrum, proving reversible reduction and oxidation without detectable formation of side products.

Quantification of reduced AQDS by iodometry. Reduced AQDS (2,6-AQH$_2$DS) was quantified via iodimetric titration in the anaerobic chamber. A standard solution of ca. 20 mM KI$_3$ was prepared as follows: iodine (254 mg, 2.0 mmol) and potassium iodide (1.66 g, 10 mmol) were dissolved in 100 mL DI water. After 2 days, the clear, dark solution was N$_2$-sparged and brought into the anaerobic chamber. The exact concentration of the KI$_3$ standard solution was quantified to be 19.5 mM via duplicate titration with sodium thiosulfate (exactly 101.5 mM, N$_2$-sparged). Procedure for the quantification of reduced AQDS in the incubations: 1000 μL anaerobic assay solution centrifuged in the anaerobic chamber+200 μL anaerobic HEPES (1.0 M, pH=7.5)+KI$_3$ standard solution as needed until color minimum, added in steps of 100 μL first, then in steps of 10 μL when closer to the equivalence point.

Control experiments without methane. Sediment incubations with AQDS (10 mM) under nitrogen did not generate substantial amounts of reduced AQDS (less than 1 mM after 3 weeks). To confirm that the methanotrophic microorganisms in the sediment had not been killed during the nitrogen+AQDS incubation, methane was later injected into these incubation bottles after 3 weeks. Upon addition of methane, AQDS was reduced at rates similar to that shown in FIG. 1.

Check for methanogenic activity. Sediment slurries were incubated under a nitrogen headspace in duplicates without an added oxidant or electron acceptor to probe for endogenous methanogenic activity. After 6 days, methane in the headspace was quantified via GC-MS (Hewlett Packard 5890 Series II gas chromatograph with mass selective detector 5972) by triplicate injections. For the first biological replicate, methane was found at a concentration that was close to the detection limit, corresponding to a specific methanogenesis rate of 0.5±0.25 nmol methane (cm$^3$ wet sediment)$^{-1}$ d$^{-1}$. For the second replicate, the methane peak was too small for accurate quantification, however, an upper limit of 0.25 nmol (cm$^3$ wet sediment)$^{-1}$ d$^{-1}$ was established. Based on these measurements, the endogenous methanogenesis rate and/or enzymatic equilibration rate is ca. 3000× lower than methane oxidation with sulfate.

Thermodynamic calculations. The standard free energy for AOM with AQDS was calculated from the corresponding redox-potentials:

$$HCO_3^- + 4H_2 + H^+ = CH_4 + 2H_2O \quad \Delta G^{\circ\prime} = -135.3 \text{ kJ mol}^{-1}$$

$$E^{\circ\prime} \text{ for } CH_4/HCO_3^- = -414 \text{ mV} - \Delta G^{\circ\prime}/(nF) = -239 \text{ mV}$$

$$E^{\circ\prime} \text{ for } 2,6\text{-}AQDS = -186 \text{ mV } [E^\circ = +228 \text{ mv}]$$

$$\Delta E^{\circ\prime} = 53 \text{ mV}, \Delta G^{\circ\prime} = -nF\Delta E^{\circ\prime} = -41 \text{ kJ mol}^{-1}$$

Incubations for FISH-nanoSIMS and RNA analysis. For AOM incubations with sulfate or AQDS that were used for nanoSIMS (FIG. 7 and FIG. 8A) and RNA analysis (FIG. 6), incubations experiments were set up following the AOM-rate measurements described above (initially containing 1.0 mM ammonium without $^{15}$N label). Methane oxidation rates were tracked in these incubations via the $^{13}$C label. After 11 days, ca. 3.5 mL of supernatant remained in the serum bottles to which 3.0 mL artificial seawater without ammonium containing either 25 mM AQDS, 28 mM sulfate, or no oxidant or electron acceptor was added. Next, 0.1 mL $^{15}$NH$_4^+$ (100 mM) was injected to yield about 2.0 mM ammonium with ca. 75% $^{15}$N. Methane oxidation was monitored. After additional 8 days, the medium of the AQDS incubations was exchanged by 5.0 mL new medium containing 25 mM AQDS and 2.0 mM $^{15}$NH$_4^+$. Now the AQDS incubations contained ca. 95% $^{15}$NH$_4^+$ in the ammonium pool. The cultures were incubated for additional 10 days before harvest. Total incubation time with labeled ammonium: 18 days. Average labeling strength: ca. 75% for sulfate and no oxidant or electron acceptor control; ca. 86% for the AQDS incubations.

For the second independent set of experiments with iron citrate, humic acids and sulfate (FIG. 8B), the medium contained 1.0 mM ammonium with ca. 40% $^{15}$N label throughout the incubation period. These experiments were carried out from identical incubations that were for the AOM rate measurements (highlighted in Table 4). In regards to Table 4, the percentage AOM rates are reported relative to sulfate-coupled AOM (1.50 μmol cm$^{-3}$ day$^{-1}$). Top: Summary of compounds described in FIG. 1B; Bottom: Oxidants or electron acceptors resulting in an AOM rate less than 0.10 μmol cm$^3$ day$^{-1}$ (<7% rel. to sulfate as oxidant or electron acceptor).

TABLE 4

List of oxidants or electron acceptors tested for AOM.

| Oxidant [conc.], replicates | $E^{\circ\prime}$ (mV) | Addition of 25 mM MoO$_4^{2-}$ | Rate relative to AOM with sulfate (%) |
|---|---|---|---|
| Sulfate [28 mM] A, B, C*, D | −220 | − | 100 |
| Sulfate [28 mM] E, F, G | | + | 20 |
| AQDS [10 mM] A, B | −186 | − | 74 |
| AQDS [10 mM] C, D | | + | 83 |
| No oxidant A, B | | − | 1.5† |
| No oxidant + H$_2$CO (4%) A, B | | − | 0 |
| 2,7-AQDS [10 mM] A, B | −185 | − | 97 |
| 1,5-AQDS [10 mM] A, B, C | −175 | − | 38 |
| Fe(III)-citrate [10 mM] A | 372 | − | 53 |
| Fe(III)-citrate [10 mM] B*, C, D | | + | 46 |
| Fe(III)-citrate [5 mM] A, B, C | | + | 37 |
| Fe(III)-citrate [2 mM] | | + | 7 |
| Fe(III)-EDTA [1.6 mM] A, B | 96 | − | 8 |
| Humic acids [1%] A*, B | n.a.‡ | − | 36 |
| Humic acids [0.5%] | | − | 26 |
| Melanin [8 mg/ml] | n.a.‡ | + | 6.4§ |
| Melanin [2 mg/ml] | | + | 4.3 |
| Melanin [0.5 mg/ml] | | + | 2.6 |
| Fe(III)-citrate [25 mM] | 372 | + | 2.5 |
| Fe(III)-NTA [1 mM] | | − | 2.5 |
| Fe(III)-NTA [10 mM] | 385 | − | ≤1.5† |
| Fe(III)-EDTA [10 mM] A, B | 96 | − | ≤1.5† |
| Phenazine methosulfate [1 mM] | 80 | − | ≤1.5† |
| Methylene blue [1 mM] | 11 | − | ≤1.5† |
| Indigo tetrasulfonate [10 mM; 1 mM] | −46 | − | ≤1.5† |
| Resazurin [10 mM] | −51 | − | ≤1.5† |
| 1-Hydroxynaphthoquinone [10 mM; 1 mM] | −137 | − | ≤1.5† |
| Phenosafranine [10 mM; 1.6 mM] | −252 | − | ≤1.5† |
| Safranine T [10 mM; 1.6 mM] | −289 | − | ≤1.5† |

*Replicate that was analyzed via nanoSIMS (see FIG. 8B and FIG. 9).

†No net methane oxidation can be deduced, because incubations without oxidant show an apparent AOM rate of 0.023 μmol cm$^{-3}$ day$^{-1}$ (1.5% relative to sulfate). This label conversion of $^{13}$CH$_4$ to $^{13}$C-DIC arises via enzyme catalyzed isotope exchange between $^{13}$CH$_4$ and DIC without net methane oxidation.

‡The midpoint reduction potentials of humic acids and melanin are not well defined. Both compounds can act as single electron acceptors due to their quinone moieties as shown experimentally for humic acids and for melanin.

§AOM occurs linearly, rates per wet sediment: with 8 mg/ml melanin: 0.096 ± 0.020 μmol cm$^{-3}$ day$^{-1}$; with 2 mg/ml melanin: 0.064 ± 0.012 μmol cm$^{-3}$ day$^{-1}$; with 0.5 mg/ml melanin: 0.039 ± 0.015 μmol cm$^{-3}$ day$^{-1}$.

Sampling for FISH-nanoSIMS and RNA. After an 18-day incubation in the presence of $^{15}$NH$_4^+$, each incubation was shaken to suspend the sediment and 1.0 mL sediment slurry was sampled using a disposable sterile needle and syringe (ca. 0.3 mL wet sediment). The sediment aliquot was briefly centrifuged (4000 rcf) in an eppendorf tube and 0.5 mL of the supernatant was removed for DIC and metabolite analysis. 0.5 mL 4% paraformaldehyde in PBS (100 mM phosphate pH=7.4, salinity=10 g $L^{-1}$) was then added to the remaining 0.5 mL sediment slurry (2% formaldehyde final), resuspended and fixed for 120 min at 4° C. The fixed sediment was subsequently washed 3 times with 1×PBS, followed by a single wash in EtOH/PBS (1:1) and then re-suspended in EtOH/PBS (1:1) to a final volume of 0.5 mL that was used for microscopy and nanoSIMS.

All remaining sediment from the identical incubations (ca. 0.7 mL wet sediment, see above) was removed for RNA analysis using a disposable sterile needle and syringe. The sediment slurry was immediately centrifuged (16000 rcf, 15 s), followed by removal of the supernatant and flash-freezing of the sediment pellet in liquid $N_2$. Frozen sediment was stored at −80° C. until RNA extraction.

RNA extraction, PCR, clone library construction, and phylogenetic analysis. RNA was extracted from the 0.7 mL frozen wet sediment described above using the RNA Powersoil Total RNA Isolation Kit (cat #12866-25; MO BIO Laboratories, Inc., Carlsbad, Calif., USA) with modifications. The eluted RNA was immediately DNase treated using the MO BIO RTS DNase Kit (cat no. 15200-50, MO BIO Laboratories, Inc., Carlsbad, Calif., USA), purified and concentrated to 24 µL using the Qiagen RNeasy Plus Micro Kit (cat #74034, Qiagen, Valencia, Calif., USA), and converted to cDNA using the Invitrogen Superscript III First-Strand Synthesis SuperMix (cat no. 18080-400, Thermo-Fisher Scientific, Grand Island, N.Y., USA) with no reverse transcriptase (NRT) controls following manufacturer's instructions. cDNA was stored at −80° C. until further processing.

PCR conditions were as follows: 1×5 PRIME HotMasterMix buffer (cat #2200400; 5 PRIME, Inc., Gaithersburg, Md., USA), 0.4 µM of each forward and reverse primer, and 1 µl of cDNA in a final volume of 25 µL. Methyl-coenzyme reductase alpha subunit (mcrA, primers ME1: GCMATGCARATHGGWATGTC (SEQ ID NO:1); ME2 TCATKGCRTAGTTDGGRTAGT (SEQ ID NO:2); and archaeal and bacterial 16S rRNA (primers Arc23F: TTCCGGTTGATCCYGCCGGA (SEQ ID NO:3) or Bac27F: AGAGTTTGATYMTGGCTC (SEQ ID NO:4) with U1492R: GGYTACCTTGTTACGACTT (SEQ ID NO:5) were amplified with 40 cycles as described in E. Trembath-Reichert et al. in Microbial Metagenomics, Metatranscriptomics, and Metaproteomics, E. F. DeLong, Ed., vol. 531, pp. 21-44. The cDNA from the sulfate microcosm was diluted 1/50 to have similar number of amplicons compared with other cDNA samples. 5 µL of the PCR products was quantified in 1% (w/v) agarose electrophoresis with SYBR safe stain under ultraviolet light, and NRT controls did not show any amplification. The remainder of the PCR product for each sample was immediately cleaned by filtration (MultiScreen PCR Filter Plate #MSNU03010, Millipore) and resuspended to the original volumes using Tris-HCl (pH 8). 1 µL of the cleaned PCR product was used per ligation reaction and cloning according instructions in the TOPO TA Cloning Kit for Sequencing using the pCR4-TOPO Vector and One Shot Top 10 chemically competent *Escherichia coli* (Life Technologies). Recombinant clones were checked for inserts by PCR, gel electrophoresis and sequenced using primers M13F (5'-GTAAAACGACGGCCAG-3' (SEQ ID NO:6)) and M13R (5'-CAGGAAACAGCTATGAC- 3' (SEQ ID NO:7)) on an ABI Prism 3730 DNA sequencer using the BigDye Terminator v3.1 cycle sequencing kit (Applied Biosystems Inc., Foster City, Calif., USA).

Sequences were manually checked and contigs assembled using the Sequencer v4.1.4 software. Sequences were then compared against the SILVA 16S rRNA database [version 119] or GenBank DNA database by using the BLAST algorithm. Alignment against reference sequences was completed using the SILVA online aligner for 16S rRNA and ClustalO for mcrA, and aligned sequences were then imported into the ARB package version 6.0.2 and manually verified. An additional 80 16S rRNA sequences were retrieved from SILVA database and 44 mcrA sequences were retrieved from NCBI Refseq and used as references for the phylogenetic analyses. The Bayesian phylogeny was generated using 1421 aligned 16S rRNA nucleic acid positions (inverse gamma rates) and 248 aligned mcrA amino acid positions (mixed amino acid model) using MrBayes v3.2.2 until split frequencies were less than 0.01. Clone library sequences fall into several clades of high phylogenetic support. Clone library sequences fall into several groups of high phylogenetic support. One representative sequence is used to represent highly similar sequences; the number of sequences represented and the representative accession number are indicated in brackets in FIG. 2. mcrA sequences were classified into groups as described by Hallam et al. (Appl Environ Microbiol 69:5483 (2003)). Clone library sequences for archaeal 16S rRNA and mcrA genes, and bacterial 16S rRNA genes were deposited in NCBI under accession numbers KU324182 to KU324260, KU324346 to KU324428, and KU324261 to KU324345, respectively.

Illumina Tag sequencing. DNA was extracted from 0.25 g of wet weight sediment using the PowerSoil DNA Isolation Kit (Cat#12888-05, Mo Bio Laboratories, Carlsbad, Calif.). PCR amplification and barcoding of the 16S rRNA gene were performed as described by O. Mason et al. (USA. Microb. Ecol. 70:766 (2015)). Amplicons for deep sequencing were outsourced to Laragen, Inc (Culver City, Calif.) and run on an Illumina MiSeq platform. Data was analyzed using QIIME 1.8.0 and processed sequences were assigned to phylotypes using a 99% similarity cutoff to the SILVA database version 115 following the procedures described in O. Mason et al.

Sample preparation for aggregate embedding, sectioning, FISH, and nanoSIMS. Sample preparation was carried out following the recently optimized protocol outlined in S. E. McGlynn et al. (*Nature* 526:531 (2015)). Briefly: Paraformaldehyde fixed consortia were detached from the sediment particles via sonication on ice with a sterile remote-tapered microtip probe (Branson) inserted into the liquid. Aggregates were concentrated on a 3 µm filter, covered in molten noble agar (2%) and embedded in glycol methacrylate (Heraeus Kulzer—Technovit® 8100). Sections of ca. 1 µm thickness were cut and stretched on a water droplet on a polylysine coated slide with teflon wells (Tekdon Inc) and analyzed by fluorescence in situ hybridization (FISH). Images of the FISH-stained consortia were collected and the location of these consortia were mapped for subsequent nanoSIMS analysis as described herein.

FISH conditions and probes. The FISH hybridization on thin sections of resin embedded microbial aggregates followed the recently optimized protocol described in S. E. McGlynn et al. The phylogenetic identity of microorganisms in the thin sections were determined using conventional FISH using oligonucleotide probes fluorescently labeled on both the 5' and 3' ends (dual labeled) as outlined herein. The FISH hybridization followed a standard protocol as described in B. M. Fuchs et al., (*Methods for general and molecular microbiology* 3:886 (2007)) and used a hybridization buffer containing 60% formamide and incubation at 46° C. for 120 min. Followed by a wash step at 48° C. for 10 min. to remove excess probes. Visualization via epifluorescence microscopy (light source EXFO, X-Cite, Series 120 Q) was accomplished by mounting the hybridized sample with a mixture of DAPI-Citifuor (5 μg DAPI/mL) and imaging with a 100× objective (Microscope Olympus BX51, objective UPlan FL N, 100×/1.30 Oil, ∞/0.17/FN 26.5). The following FISH probes were used (final concentration 2.5 ng/μL for each): S-D-Arch-0915-a-A-20 in FITC, dual labeled: 5' to 3'=GTGCTCCCCCGCCAATTCCT (SEQ ID NO:8); S-*-ANME2c-0760-a-A-18 in Cy3, dual labeled: 5' to 3'=CGCCCCCAGCTTTCGTCC (SEQ ID NO:9); and S-*-Dsb-0658-a-A-18 in Cy5, dual labeled: 5' to 3'=TCCACTTCCCTCTCCCAT (SEQ ID NO:10). The overlay figures (FIG. 7 and FIGS. 9-11) were contrast-adjusted for display purposes. FITC channel (Arc 915) is not shown. For aggregates that were positively stained for both, ANME-2c and for DSS, the DAPI channel was omitted for the overlay image.

nanoSIMS procedures and parameters. After FISH and mapping, the glass slides were scored and broken to size to fit in the Cameca "Geology" holder for the nanoSIMS, and coated with 50 nM gold to enhance conductivity. Secondary ion mass spectrometry analysis was carried out on a nanoSIMS 50 L instrument (Cameca) using a primary $Cs^+$ ion beam. Pre-sputtering of target consortia was conducted with 100 pA current at D1=1 until 70,000-1,000,000 counts were reached on the $^{12}C$ detector. Analytical conditions included a 256×256 raster (or 512×512 raster for frames larger than 35 μm), ES=2, D1=4 (0.5 pA of current). Chained analyses were set up using SIBC, EOS, and HMR automatic peak centering every 2 frames using the $^{14}N^{12}C^-$ ion as reference. The following secondary ions were collected during the analysis: $^{12}C^-$, $^{13}C^-$, $^{12}C^{14}N^-$, $^{12}C^{15}N^-$, $^{32}S^-$, $^{33}S^-$ and $^{34}S^-$. 1-4 frames were collected for each aggregate. The ions $^{12}C^{14}N^-$ and $^{12}C^{15}N^-$ were used for the fractional abundances of $^{15}N$ reported herein.

nanoSIMS data processing. Raw nanoSIMS data files were initially processed in the Matlab-based program Look@NanoSIMS to align and accumulate frames and extract ion count data. FISH images of aggregates were used to define regions of interest (ROIs) on the nanoSIMS ion images that correspond to archaeal or bacterial biomass. Total ion counts in each ROI for $^{12}C^{15}N^-$ and $^{12}C^{14}N^-$ were used to calculate partner-specific relative biosynthetic activity ($^{15}N/(^{14}N+^{15}N)$) for each aggregate (data for FIGS. 8A and 8B). For display purposes the median image filter medfilt2 from the Matlab Image Processing Toolbox was applied to the images of aggregate fractional abundance $^{15}N$ to reduce the noise of abnormally bright pixels. This filter was not applied to the raw data for any analyses.

Calculation of doubling times from average cellular $^{15}N$ after 18 days ($^{15}F_{18days}$):

Fraction of new biomass: $\chi=[B_{18\ days}-B_0]/B_{18\ days}$

With exponential growth: $\chi=1-\exp(-\mu*18\ days)$

With $^{15}F_0 \approx 0$: $^{15}F_{18\ days}=\chi*^{15}F_{NH_4^+}$

Specific growth rate: $\mu=-\ln(1-^{15}F_{18\ days}/^{15}F\ NH_4^+)/18\ days$

Doubling time: $t_d=\ln(2)/\mu$ $^{15}F_{NH_4^+}=0.75$ for sulfate and 0.86 for AQDS Quantification of AOM with AQDS. To quantify AOM with AQDS, anaerobic microcosm experiments were performed using methane seep sediment from the Santa Monica basin that had been rendered sulfate- and sulfide-free and amended with 50 mmol AQDS and $^{13}C$-labeled methane [0.35 MPa]. After a 21-day incubation at 4° C., approximately 12.5 mmol of dissolved inorganic carbon (DIC) formed from the $^{13}C$-methane (see FIG. 1A), concomitant with the reduction of AQDS close to the predicted 1:4 stoichiometry (see Table 2).

The initial rates of AOM with AQDS were equivalent to the rates measured with sulfate over the first 6 days (see FIG. 1B) and later diverged as the AQDS was depleted from solution. At 22.5° C., where AQDS has higher solubility (Table 3), the AOM rates with AQDS exceeded those with sulfate (see FIG. 4).

To confirm that the observed methane oxidation with AQDS was not coupled to traces of sulfate, AOM was tracked in the presence of sodium molybdate, a competitive inhibitor for sulfate reduction. With the addition of 25 mM molybdate, rates of sulfate-coupled AOM decreased by approximately fivefold relative to controls, which is consistent with previous reports. The high rates of methane oxidation in the sulfate-free incubations containing AQDS showed no inhibitory response if molybdate was included, indicating a decoupling of AOM from sulfate reduction (see FIG. 1A-B).

Stimulation of AOM without sulfate is not restricted to AQDS. Regioisomers of AQDS (1,5-AQDS and 2,7-AQDS), humic acids, and soluble iron(III) complexes (ferric citrate and ferric-EDTA) also stimulated anaerobic oxidation of methane at rates that were at least 0.1 mmol $cm^{-3}$ $day^{-1}$ (see FIG. 1B; a list of all oxidants or electron acceptors tested is provided in Table 4). In control incubations without an added electron acceptor, a small apparent methane oxidation activity (1.5% relative too sulfate-coupled AOM, see FIG. 1B) was measured that is probably attributed to enzyme-catalyzed isotope exchange between methane and DIC without net methane oxidation. In killed control experiments (formaldehyde addition), no conversion of $^{13}C$-methane to DIC was detected (see FIG. 1B).

The archaeal 16S ribosomal RNA (rRNA) gene diversity of the seep sediment used in the AOM microcosm experiments was dominated by ANME-2 of the subgroups ANME-2a and ANME-2c, with a low relative abundance of ANME-1 phylotypes (see FIG. 5). To identify the active archaea potentially involved in methane oxidation in the experiments, after 4 weeks, expressed archaeal 16S rRNA and the alpha subunit of the methyl coenzyme M reductase (mcrA) were sequenced from microcosm treatments containing either sulfate, AQDS, or no added electron acceptor. The archaeal sequences recovered from the 16S rRNA and mcrA cDNA clone libraries were similar in the three treatments, with each containing only representatives of ANME-2a and -2c (see FIG. 6). The detection of transcripts from multiple subgroups of ANME-2 in each treatment suggests that the same ANME lineages are active in AOM, independent of whether sulfate or AQDS is supplied as the oxidant or electron acceptor. In contrast to the similar ANME composition, the relative abundance of recovered bacterial SRB clones (e.g. Desulfobacteraceae SEEP-SRB1) in the cDNA libraries decreased in treatments lacking sulfate as compared to microcosms supporting active sulfate-coupled AOM (see Table 5), and suggests that ANME may be capable of using AQDS directly without syntrophic interaction.

sortia from two sets of experiments (n=20 and n=19 consortia) was positively correlated at a ratio of approximately 1:1, indicating balanced syntrophic growth during AOM

TABLE 5

Bacterial 16S rRNA diversity.

| Bacterial 16S cDNA sequences recovered* | Oxidant/electron acceptor | | |
|---|---|---|---|
| | Sulfate | AQDS† | none |
| Proteobacteria/Deltaproteobacteria/ Desulfobacterales_Desulfobacteraceae/SEEP-SRB1 | 18 | 2 | 0 |
| Proteobacteria/Deltaproteobacteria/Desulfuromonadales/ Desulfuromonadaceae_Pelobacter_2 | 2 | 3 | 0 |
| Bacteroidetes/Sphingobacteriia_Sphingobacteriales_1/WCHB1-69 | 2 | 0 | 0 |
| Chlorobi/Ignavibacteria_Ignavibacteriales/BSV26 | 2 | 0 | 0 |
| Proteobacteria/Deltaproteobacteria/ Desulfarculales_Desulfarculaceae/uncultured | 2 | 0 | 0 |
| Proteobacteria/Gammaproteobacteria_1/ Pseudomonadales_Pseudomonadaceae/Pseudomonas_1 | 1 | 3 | 0 |
| Chloroflexi/Anaerolineae_Anaerolineales_Anaerolineaceae/uncultured | 1 | 1 | 1 |
| Proteobacteria/Deltaproteobacteria/Sva0485 | 1 | 1 | 0 |
| Acidobacteria/Subgroup 22 | 1 | 0 | 0 |
| Candidate division OP8 | 1 | 0 | 1 |
| Proteobacteria/Deltaproteobacteria/Sh765B-TzT-29 | 1 | 0 | 0 |
| Proteobacteria_Deltaproteobacteria_Desulfobacterales_Nitrospinaceae/ uncultured | 1 | 0 | 0 |
| Spirochaetae_Spirochaetes/Spirochaetales/Spirochaetaceae/Spirochaeta_2 | 0 | 9 | 1 |
| Proteobacteria/Betaproteobacteria/Burkholderiales/ Oxalobacteraceae/Herbaspirillum_1 | 0 | 4 | 0 |
| Candidate division JS1 | 0 | 2 | 3 |
| Proteobacteria/Epsilonproteobacteria/ Campylobacterales_Helicobacteraceae/Sulfurimonas | 0 | 2 | 1 |
| Bacteroidetes/Flavobacteriia_Flavobacteriales/ Flavobacteriaceae_1/Maritimimonas | 0 | 1 | 0 |
| Chloroflexi/Ardenticatenia/uncultured | 0 | 1 | 1 |
| Firmicutes_Clostridia_1/Clostridiales/Family XII/Fusibacter | 0 | 1 | 0 |
| Proteobacteria/Alphaproteobacteria/Rhizobiales_1/ Brucellaceae/Ochrobactrum_1 | 0 | 1 | 0 |
| Actinobacteria/Acidimicrobiia_Acidimicrobiales/OM1 clade | 0 | 0 | 3 |
| Bacteroidetes/BD2-2 | 0 | 0 | 2 |
| Bacteroidetes/Bacteroidia_Bacteroidales/ Porphyromonadaceae_4/uncultured | 0 | 0 | 1 |
| Candidate division WS3 | 0 | 0 | 1 |
| Chloroflexi/Dehalococcoidia/GIF9 | 0 | 0 | 1 |
| Lentisphaerae/B01R017 | 0 | 0 | 1 |
| Planctomycetes/Phycisphaerae/MSBL9 | 0 | 0 | 1 |
| Planctomycetes/Phycisphaerae/Phycisphaerales/ AKAU3564 sedimentgroup | 0 | 0 | 1 |
| Proteobacteria/Gammaproteobacteria_2/ Chromatiales_Ectothiorhodospiraceae_Acidiferrobacter | 0 | 0 | 1 |
| Spirochaetae_Spirochaetes/Spirochaetales/Leptospiraceae/uncultured | 0 | 0 | 1 |
| TOTAL NUM OF CLONES | 33 | 31 | 21 |

*Data based on 16S cDNA clone libraries.
†PCR amplification and cloning of bacterial cDNA from the AQDS treatment was challenging due to weak amplification, few insert containing clones, and chimeric sequences.

Cell-specific stable isotope analysis was used to quantify the anabolic activity of ANME-2 (including ANME-2c) and their co-associated syntrophic partners in consortia recovered from incubations supplied with different oxidants or electron acceptor (including sulfate, AQDS, humic acids, and ferric iron). Using $^{15}NH_4^+$ stable isotope probing combined with fluorescence in situ hybridization and nanoscale secondary ion mass spectrometry [FISH-SIMS], the cell-specific anabolic activity ($^{15}N$ cellular enrichment) was measured in paired ANME and SRB populations in consortia. After 18 days of incubation with $^{15}NH_4^+$, consortia were phylogenetically identified by FISH using ANME-2c and Desulfobacteraceae-targeted oligonucleotide probes and were analyzed by nanoSIMS to quantify the assimilation of $^{15}NH_4^+$ for each paired population of ANME-2 and SRB.

In AOM microcosms containing sulfate, the $^{15}NH_4^+$ assimilation by co-associated bacteria and archaea in con- (see FIG. 7C and FIG. 8A-B). ANME-SRB consortia recovered from sulfate-free incubations amended with AQDS also showed high levels of $^{15}NH_4^+$ assimilation; however, in this case, anabolic activity within each of these consortia occurred only in the ANME archaea and not in their co-associated bacterial partners (see FIG. 7F and FIG. 8A). This is consistent with the weak FISH signal observed for the Desulfobacteraceae. The data offer direct validation of the results based on RNA analysis, demonstrating that when AQDS was supplied as the terminal electron acceptor for AOM, the ANME-2 archaea sustained active biosynthesis that was decoupled from the activity of the SRB partner. This was directly shown for ANME-2c (n=11 consortia) and inferred for ANME-2a on the basis of nanoSIMS results from the eight non-ANME-2c aggregates that were all anabolically active. Consortia from incubations with methane and $^{15}NH_4^+$, but lacking an electron acceptor, showed no measurable anabolic activity in either partner (n=9 ANME-SRB consortia; see FIG. 8A, inset, and FIG. 10).

The ANME cells paired with SRB in consortia from AQDS incubations showed similar levels of anabolic activity [3.3 months doubling time based on average $^{15}$N-incorporation] as those of ANME archaea conserving energy through conventional sulfate-coupled AOM [2.9 months doubling time] in parallel incubations, suggesting equivalent potential for growth (see FIG. 8A). Apparently, ANME-2 archaea are capable of conserving energy for biosynthesis independent of sulfate availability and separated from the activity of their syntrophic bacterial partners.

AOM incubations with iron(III)-citrate and humic acids as the alternative electron acceptors also demonstrated exclusive biosynthetic activity of ANME-2c and other ANME-2 cells (see FIG. 8B and FIG. 9). In contrast to incubations with sulfate or AQDS, only a few and mostly small AOM consortia [14 out of 31 for iron(III)-citrate and 4 out of 46 for humic acids] were anabolically active (>10% archaeal activity relative to cells in the sulfate treatments, or >0.8 atomic % (at %) of 15N), despite the high rates of AOM measured with those compounds (see FIG. 1B).

Certain embodiments of the invention have been described. It will be understood that various modifications may be made without departing from the spirit and scope of the invention. Other embodiments are within the scope of the following claims.

What is claimed is:

1. A bioelectrochemical device comprising:

a methane source to provide methane to the bioelectrochemical device;

an aqueous solvent system that comprises an aqueous redox-active soluble electron acceptor that is re-circulated in the bioelectrochemical device, wherein the aqueous redox-active soluble electron acceptor is selected from the group consisting of 2,6-AQDS (9,10-anthraquinone-2,6-disulfonate), 2,7-AQDS (9,10-anthraquinone-2,7-disulfonate), 1,5-AQDS (9,10-anthraquinone-1,5-disulfonate), Fe(III)-citrate, Fe(III)-EDTA, humic acids, and melanin;

a bioreactor comprising one or more different types of $C_1$-metabolizing microorganisms that are capable of metabolizing methane and reducing the aqueous redox-active soluble electron acceptor to a reduced electron acceptor;

a fuel cell comprising:

an anode that can oxidize the reduced electron acceptor back to the electron acceptor, a cathode that can reduce an oxidant, and an ion conductor placed between the cathode and anode, wherein the ion conductor selectively transports positively or negatively charged ions.

2. The bioelectrochemical device of claim 1, wherein the bioelectrochemical device further comprises one or more of the following:
- a series of tubes that are fluidly in contact with the bioreactor and the fuel cell;
- a pump that powers the recirculation of the solvent system;
- a check valve that selectively allows the passage of methane into the bioelectrochemical device;
- a set of valves and inlets that are fluidly in contact with the aqueous solvent system that allow for addition or adjustment of the aqueous solvent system; and/or
- a $CO_2$ extraction device that removes dissolved $CO_2$ from the aqueous solvent system.

3. The bioelectrochemical device of claim 2, wherein the bioelectrochemical device comprises:
- the pump that powers the recirculation of the solvent system;
- the check valve that selectively allows the passage of methane into the bioelectrochemical device;
- the set of valves and inlets that are fluidly in contact with the aqueous solvent system that allow for addition or adjustment of the aqueous solvent system;
- the $CO_2$ extraction device that removes dissolved $CO_2$ from the aqueous solvent system; and/or
- the series of tubes that are fluidly in contact with the bioreactor, and the fuel cell, wherein the series of tubes are also fluidly in contact with the pump, the check valve, the set of valves and inlets/outlets, and the $CO_2$ extraction device.

4. The bioelectrochemical device of claim 1, wherein the one or more different types of $C_1$-metabolizing microorganisms are methanogens, methanotrophs, and/or a recombinantly engineered organism(s) that are capable of oxidizing methane.

5. The bioelectrochemical device of claim 1, wherein the one or more different types of $C_1$-metabolizing microorganisms are anaerobic methanotrophs; and wherein the aqueous solvent is substantially free or devoid of dissolved oxygen.

6. The bioelectrochemical device of claim 1, wherein the methane source is a methane producing fermentation system utilizing biomass, coal, human waste, and/or animal waste as a fuel source, and/or a purified fuel gas stream that is enriched with methane.

7. The bioelectrochemical device of claim 1, wherein the aqueous redox-active soluble electron acceptor is a single-electron acceptor with a standard reduction potential more positive than ca. -240 mV.

8. The bioelectrochemical device of claim 1, wherein the aqueous solvent system further comprises one or more of the following: buffers, salts, and/or nutrients.

9. The bioelectrochemical device of claim 1, wherein the bioreactor comprises:
- a housing with two surfaces an inner surface that comes into contact with the aqueous solvent and an outer surface that does not come into contact with the aqueous solvent;
- at least two ports to allow for the aqueous solvent to enter the bioreactor and to allow for the aqueous solvent to exit the bioreactor.

10. The bioelectrochemical device of claim 9, wherein the bioreactor comprises one or more $C_1$-metabolizing microorganisms that are grown or contained within a bed of media or solid support(s).

11. The bioelectrochemical device of claim 10, wherein the media and solid support comprises a high surface area so that $C_1$-metabolizing microorganisms can spread across the surface of the media or the solid support.

12. The bioelectrochemical device of claim 11, wherein the solid support is comprised of a porous or very porous material.

13. The bioelectrochemical device of claim 9, wherein the bioreactor further comprises filters or membranes that prevent the passage of $C_1$-metabolizing microorganisms or cellular debris out of the bioreactor.

14. The bioelectrochemical device of claim 1, wherein the aqueous solvent flows into the top of the fuel cell and exits out the bottom of the fuel cell.

15. The bioelectrochemical device of claim 1, wherein the aqueous solvent flows into the bottom of the bioreactor and exits out the top of the bioreactor.

16. The bioelectrochemical device of claim 1, wherein the anode and cathode of the fuel cell comprise of electrodes made of carbon or metals such as titanium, and modified by coating with platinum or platinum ruthenium alloys as catalysts; and wherein the ion conductor includes but not limited to a sulfonated tetrafluoroethylene based fluoropolymer-copolymer membrane.

17. The bioelectrochemical device of claim 2, wherein the $CO_2$ extraction device is a membrane degasifier device or $CO_2$-precipitating chemical reactor.

18. The bioelectrochemical device of claim 3, wherein the pump, check valve and $CO_2$ extraction device are electronically controlled directly and/or controlled remotely over a network or wireless communication using a computer, cell phone, and/or tablet.

19. A method to produce direct electrical current comprising providing methane to the bioelectrochemical device of claim 1.

* * * * *